US012656340B2

(12) United States Patent
Gombrich et al.

(10) Patent No.: US 12,656,340 B2
(45) Date of Patent: *Jun. 16, 2026

(54) DIAGNOSTICS METHOD FOR DETECTING MICROPARTICLES

(71) Applicant: SHERO DIAGNOSTICS, San Jose, CA (US)

(72) Inventors: Matthew Gombrich, Underhill, VT (US); Shervin Javadi, San Jose, CA (US)

(73) Assignee: SHERO DIAGNOSTICS, San Jose, CA (US)

( * ) Notice: Subject to any disclaimer, the term of this patent is extended or adjusted under 35 U.S.C. 154(b) by 1355 days.

This patent is subject to a terminal disclaimer.

(21) Appl. No.: 17/314,799

(22) Filed: May 7, 2021

(65) Prior Publication Data

US 2021/0349081 A1     Nov. 11, 2021

Related U.S. Application Data

(60) Provisional application No. 63/022,287, filed on May 8, 2020, provisional application No. 63/061,729, filed on Aug. 5, 2020.

(51) Int. Cl.
| | |
|---|---|
| *G01N 33/543* | (2006.01) |
| *G01N 15/14* | (2024.01) |
| *G01N 33/569* | (2006.01) |

(52) U.S. Cl.
CPC . *G01N 33/54313* (2013.01); *G01N 33/56983* (2013.01); *G01N 15/14* (2013.01); *G01N 2015/1402* (2013.01); *G01N 2333/165* (2013.01)

(58) Field of Classification Search
CPC ....... G01N 33/54313; G01N 33/56983; G01N 15/14; G01N 2015/1402; G01N 2333/165; G01N 33/54346
See application file for complete search history.

(56) References Cited

PUBLICATIONS

Dalili, Arash et al. "A review of sorting, separation and isolation of cells and microbeads for biomedical applications: microfluidic approaches." The Analyst vol. 144, 1 (2018): 87-113. doi:10.1039/c8an01061g (Year: 2018).*

Yang, Sung-Yi et al. "Micro flow cytometry utilizing a magnetic bead-based immunoassay for rapid virus detection." Biosensors & bioelectronics vol. 24,4 (2008): 861-8. doi:10.1016/j.bios.2008.07.019 (Year: 2008).*

Reddy, Tyler, and Mark S P Sansom. "The Role of the Membrane in the Structure and Biophysical Robustness of the Dengue Virion Envelope." Structure (London, England : 1993) vol. 24,3 (2016): 375-82. doi:10.1016/j.str.2015.12.011 (Year: 2016).*

Barteneva, Natasha S et al. "Circulating microparticles: square the circle." BMC cell biology vol. 14 23. Apr. 22, 2013, doi:10.1186/1471-2121-14-23 (Year: 2013).*

Yan, Ying et al. "Laboratory testing of SARS-CoV, MERS-CoV, and SARS-CoV-2 (2019-nCoV): Current status, challenges, and countermeasures." Reviews in medical virology vol. 30,3 (2020): e2106. doi:10.1002/rmv.2106 (Year: 2020).*

Zeineldin, Reema et al. "Superquenching as a detector for microsphere-based flow cytometric assays." Cytometry. Part A : the journal of the International Society for Analytical Cytology vol. 69,5 (2006): 335-41. doi:10.1002/cyto.a.20250 (Year: 2006).*

Staats, J., Divekar, A., McCoy, J.P., Maecker, H.T. (2019). Guidelines for Gating Flow Cytometry Data for Immunological Assays. In: McCoy, Jr, J. (eds) Immunophenotyping. Methods in Molecular Biology, vol. 2032. Humana, New York, NY. https://doi.org/10.1007/978-1-4939-9650-6_5 (Year: 2019).*

Wang, Sida et al. "Bead mediated separation of microparticles in droplets." PloS one vol. 12,3 e0173479. Mar. 10, 2017, doi:10.1371/journal.pone.0173479 (Year: 2017).*

* cited by examiner

*Primary Examiner* — Gregory S Emch
*Assistant Examiner* — McKenzie A Dunn
(74) *Attorney, Agent, or Firm* — Kilpatrick Townsend & Stockton LLP

(57) ABSTRACT

The methods, compositions and systems provided herein use functionalized beads to detect a target microparticle in a test sample, the method comprising (a) contacting the test sample containing the target microparticle with a plurality of functionalized beads. The size of the target microparticle is less than 1 μm. The functionalized beads comprise beads coated with molecules of a capture agent, and at least some molecules of the capture agent bind to the target microparticle, thereby forming target microparticle-loaded beads comprising the functionalized beads and the target microparticle. The method further comprises (b) detecting the target microparticle-loaded beads using a flow cytometer, thereby detecting the presence of the target microparticle in the test sample, and the target microparticle-loaded the beads are detected with the detection limit that ranges from 10 microparticles per ml to 10e4 microparticles per ml.

21 Claims, 7 Drawing Sheets

Low-Level Functionalization

High-Level Functionalization with Increased Viral Capture

Assay Gating Strategy (Negative)

Side Scatter

Forward Scatter

Positive/Negative Threshold
FL3 Triggered off of Bead Gate

Assay Gating Strategy For Positive SARS-CoV-2

DIAGNOSTICS METHOD FOR DETECTING MICROPARTICLES

CROSS REFERENCE TO RELATED APPLICATIONS

This application claims priority to U.S. Provisional Application No. 63/022,287, filed on May 8, 2020, and U.S. Provisional Application No. 63/061,729, filed on Aug. 5, 2020. The entire disclosure of each of the aforementioned provisional applications is herein incorporated by reference for all purposes.

FIELD OF THE INVENTION

The present invention relates to a method of detecting a variety of microparticles including but not limited to viruses, bacteria, extra cellular vesicles and minicells. The method of detecting can be used for diagnostics, research or other applications.

BACKGROUND OF THE INVENTION

There is a strong interest in improving speed and sensitivity for detection of microparticles in environmental and clinical samples. In particular, the emergence of the 2019-2020 COVID-19 pandemic presents a clinical situation where rapid determination of a patient's viral status is of the upmost importance (Zhang et al., 2020; Wang et la., 2020; and Huang et al., 2020).

Current approved methodologies rely heavily on RT-PCR for the determination of the target microparticle (e.g., SARS-COV-2) to diagnose the disease (CDC: Interim Guidelines). This method has relatively low sensitivity and specificity. For example, current estimates show the sensitivity and specificity of this RT-PCR based method for detection of SARS-COV-2 are 30-80% and 79%, respectively (www.cdc.gov/coronavirus/2019-nCoV/lab/guidelines-clinical-specimens.html). In addition, genotypic diagnostic methodology can provide false results in cases of minor mutations of the pathogen or the lingering presence of DNA or RNA fragments associated from a previous infection which the patient has recovered from. This suboptimal performance will have clinical consequences both for this current pandemic and any future outbreaks that may occur. In addition, the relatively low certainty associated with current methods may have significant negative impact on socioeconomic policies that heavily rely on statistical data on the pandemic's spread and associated mortality rate.

Although methods of detecting microparticles that are based on phenotypes rather than genotypes relied on by PCR have been explored, they are not effective as the small size of the pathogens makes them very difficult to detect using other diagnostic methods such as flow cytometry. As such, there remains a need for a method which does not rely on the specific DNA or RNA composition of the particle and uses phenotypic characteristics for detection.

Further, since exposure to more novel pathogens such as Ebola, Zika and other variants of COVID-19 remain a distinct threat, it is important for the method to detect the presence of microorganisms and microparticles across a wide range of pathogens and other discrete etiologies. There remains a need for a diagnostic method that is not be limited to detecting only specific viral infections but rather covers a wide range of pathogens.

BRIEF SUMMARY OF THE INVENTION

The methods, compositions and systems provided herein use functionalized beads to amplify a particle-specific phenotypic signal to levels detectable by devices, such as a flow cytometer. This method is also capable of being multiplexed to detect a sample composed of several types of microparticles simultaneously. In addition, because this method is not based on the DNA or RNA sequence of the microparticle, it will not be susceptible to false readings caused by minor mutations or presence of DNA or RNA fragments in the sample.

In one aspect, this disclosure provides a method of detecting a target microparticle in a test sample, the method comprising (a) contacting the test sample containing the target microparticle with a plurality of functionalized beads. The size of the target microparticle is less than 1 μm. The functionalized beads comprise beads coated with molecules of a capture agent, and at least some molecules of the capture agent bind to the target microparticle, thereby forming target microparticle-loaded beads comprising the functionalized beads and the target microparticle. The method further comprises (b) detecting the target microparticle-loaded beads using a flow cytometer, thereby detecting the presence of the target microparticle in the test sample, and the target microparticle-loaded beads are detected with a detection limit that ranges from 10 microparticles per ml to 10e4 microparticles per ml.

In some embodiments, the method further comprises contacting the test sample with a secondary reagent before step (a), wherein the secondary reagent binds to the microparticle and said binding is capable of producing a detectable signal in a detection channel of the flow cytometer. In some embodiments, the method further comprises after step (a) but before (b), contacting the target microparticle-loaded beads with a secondary reagent, and the secondary reagent binds the microparticle, and the binding produces a detectable signal in a detection channel of the flow cytometer. In some embodiments, the secondary reagent specifically binds to a surface component on the microparticle. In some embodiments, the secondary reagent and capture agents bind to different surface components on the microparticle.

In some embodiments, the microparticle is a SARS-COV-2 viral particle, which comprises membrane lipids and nucleic acids, and the secondary reagent intercalates to the nucleic acids or the lipids. In some embodiments, the secondary reagent is a member selected from the group consisting of a cell-permeant, an RNA-specific dye and a lipophilic carbocyanine dye.

In some embodiments, the functionalized beads are capable of emitting a detectable signal, and step (a) of the method further comprises adding a quencher to the test sample and the quencher is capable of binding to the functionalized beads in the absence of the target microparticle. The binding quenches the detectable signal from the functionalized beads. In some embodiments, the quencher binds to the functionalized beads with less affinity than the target microparticle does. In some embodiments, the quencher binds to the functionalized beads through binding to the capture agents on the functionalized beads, thus reducing or eliminating the bead fluorescence. In some embodiments, the presence of the target microparticle in the sample displaces the quencher from binding to the functionalized beads.

In some embodiments, detecting the target microparticle-loaded beads in the test sample comprises: (1) (i) analyzing a calibration sample comprising functionalized beads with or without the secondary reagent using the flow cytometer, wherein the beads and functionalized beads in the calibration sample are of the same type as the beads and functionalized beads used to analyze the test sample in step (a), and wherein the calibration sample does not comprise the target microparticle, (ii) collecting signals from the scatter and/or fluorescence channels, (iii) determining relative positions of the functionalized beads in a flow cytometry plot displaying the scatter and/or fluorescence channels, and selecting at least one gate that includes only functionalized beads and excludes other particles, and (iv) determining a threshold that is greater than the signal from the detection channel for the calibration sample based on the at least one gate. The method further comprises (2) analyzing the test sample that has contacted the functionalized beads using the flow cytometer; and (3) detecting the signal generated from the detection channel for the test sample that has contacted the functionalized beads based on the at least one gate, wherein the signal is sufficiently greater than the threshold, thereby detecting the target microparticle.

In some embodiments, detecting the target microparticle-loaded beads in the test sample comprises: (1) (i) analyzing a calibration sample comprising functionalized beads and the quencher using the flow cytometer, wherein the functionalized beads in the calibration sample are of the same type as the functionalized beads used to analyze the test sample in step (a), and wherein the calibration sample does not comprise the target microparticle; (ii) collecting signals from the scatter and/or fluorescence channels, (iii) determining relative positions of the functionalized beads in a flow cytometry plot and selecting a gate that includes the functionalized beads and excludes other particles including, but not limited to, cells and debris, and (iv) determining a threshold that is greater than the signal from the detection channel for the calibration sample based on the gate. The method further comprises (2) analyzing the test sample that has contacted the functionalized beads using the flow cytometer; and (3) detecting the signal generated from the detection channel for the test sample that has contacted the functionalized beads based on the gate, wherein the signal is sufficiently greater than the threshold, thereby detecting the target microparticle.

In some embodiments, the target microparticle is a member selected from the group consisting of a virus, a viral particle, a bacterium, a minicell, an exosome, and a microvesicle. In some embodiments, the target microparticle is present in the test sample in a concentration that ranges from about 10e1 to about 10e7 of the target microparticle per milliliter. In some embodiments, the target microparticle is a SARS-COV-2 virus or part thereof.

In some embodiments, the capture agent binds to the S protein on the SARS-COV-2 virus.

In some embodiments, the bead is a latex bead. In some embodiments, the bead has a diameter of 10 nm to 10,000 nm. In some embodiments, 1% to 100% of the surface of the beads is covered with the capture agents. In some embodiments, the bead is capable of emitting auto-fluorescence. In some embodiments, each bead is coated with 1-10e6 capture agent molecules. In some embodiments, the bead is capable of emitting fluorescence. In some embodiments, the capture agent is a member selected from the group consisting of a polypeptide, an antibody or binding portion thereof, a nucleic acid, an aptamer, and a phage.

The capture agent may be linked to the bead through non-covalent coupling or covalent linkage. In some embodiments, the capture agent is covalently linked to the bead via a covalent bond formed between a carboxyl group and an amino group. In some embodiments, the step of contacting the test sample with a functionalized bead comprises incubating the test sample with the functionalized bead for a period of time that ranges from about 1 to about 60 minutes. In some embodiments the contacting step comprises contacting the test sample with a plurality of functionalized beads in a reaction solution, and the functionalized beads are present in the reaction solution in a concentration that ranges from about 10 to about 1,000 per µl.

In some embodiments the contacting step comprises contacting the test sample with a solution comprising a plurality of functionalized beads, wherein the functionalized beads are present in an amount such that the amount ratio of the target microparticle to the functionalized beads ranges from 5 to 10e9. In some embodiments, after an initial analysis based on scatter and/or fluorescence signals, the method comprises using Boolean logic to automatically adjust and optimize the concentration the functionalized beads, the concentration of microparticles in the test sample, or the concentration of the secondary reagent. In some embodiments, the optimizing includes optimizing the concentration ratio between the functionalized beads and the microparticles in the test sample.

Also provided in this disclosure is a method of screening for a compound that can block a target microparticle contained in a test sample from binding to its cognate receptor, the method comprises: (a) contacting the test sample containing the target microparticle with a plurality of functionalized beads and a potential blocking agent to produce a treated test sample, wherein the size of the target microparticle is less than 2 µm, wherein the functionalized beads comprise beads coated with the cognate receptor molecules, and wherein the binding of the functionalized beads to the target microparticle results in a signal that is a detectable by flow cytometer; and (b) analyzing the treated test sample using a flow cytometer, and (c) determining that the blocking agent can block binding of the microparticle to its cognate receptor if the signal resulted from binding of the functionalized beads to the target microparticle is not detected, or determining the blocking agent cannot block binding of the microparticle to its cognate receptor if the signal resulted from binding of the functionalized beads to the target microparticle is detected.

In some embodiments the test sample is a throat swab sample, a nasal swab sample, or a sputum sample from a patient.

Also provided in this disclosure is a method of detecting at least two different target microparticles in a test sample, the method comprising: (a) contacting the test sample with a plurality of functionalized beads, wherein the functionalized beads comprise beads coated with at least two capture agents, each recognizing a different target microparticle, wherein, for each of the capture agents, at least some molecules of the capture agent bind to their cognate target microparticle, thereby forming target microparticle-loaded beads comprising the functionalized beads and the cognate target microparticle, thereby forming at least two different target microparticle-loaded beads; and (b) detecting the at least two different target microparticle-loaded beads using a flow cytometer, thereby detecting the presence of the at least two different target microparticles in the test sample. In some embodiments, the at least two different target microparticle-loaded beads are capable of producing fluorescence that can be detected at different detection channels of the flow cytometer. In some embodiments, the at least two different target microparticles comprise a SARS-COV-2 virus and an influenza virus.

Also provided herein is a kit for detecting a target microparticle in a test sample, wherein the kit comprises a plurality of functionalized beads, wherein each of at least some of the functionalized beads is coated with one or more capture agents; and wherein the one or more capture agents are capable of binding to the target microparticle. In some embodiments the kit further comprises a secondary reagent, wherein the secondary reagent is capable of binding to the target microparticle, and said binding produces a detectable signal in a detection channel of a flow cytometer. In some embodiments, the plurality of functionalized beads emit fluorescence, and the kit further comprises a quencher, wherein the quencher is capable of binding to the functionalized beads, and wherein said binding quenches the fluorescence in the absence of the target microparticle.

Also provided herein is a system for detecting target microparticle in a test sample, wherein the system comprises: a component for loading the test sample; a plurality of functionalized beads, wherein each of at least some of the functionalized beads is coated with one or more capture agents, wherein the one or more capture agents are capable of binding to the target microparticles; and a flow cytometer for detecting the binding between the target microparticle and the functionalized beads.

Also provided herein is a method of detecting a target microparticle in more than one test samples, wherein the more than one test samples comprise a first test sample and a second test sample, the method comprising: (a) contacting the first test sample with first functionalized beads, and contacting the second test sample with second functionalized beads, wherein the first functionalized beads and the second functionalized beads are distinguishable in size, fluorescence characteristics, or a combination of both, wherein the first and the second functionalized beads are coated with a capture agent recognizing the target microparticle, wherein at least some molecules of the capture agent in the first functionalized beads bind to the target microparticle in the first test sample to form first target microparticle-loaded beads, and wherein at least some molecules of the capture agent in the second functionalized beads bind to the target microparticle in the second test sample to form second target microparticle-loaded beads. The method further comprises (b) combining the first target microparticle-loaded beads and the second target microparticle-loaded beads in one single reaction, and (c) detecting the first and the second target microparticle-loaded beads, thereby detecting the presence of the target microparticles in the first test sample and the second test sample, respectively.

DETAILED DESCRIPTION

1. Definitions

Figure 1:
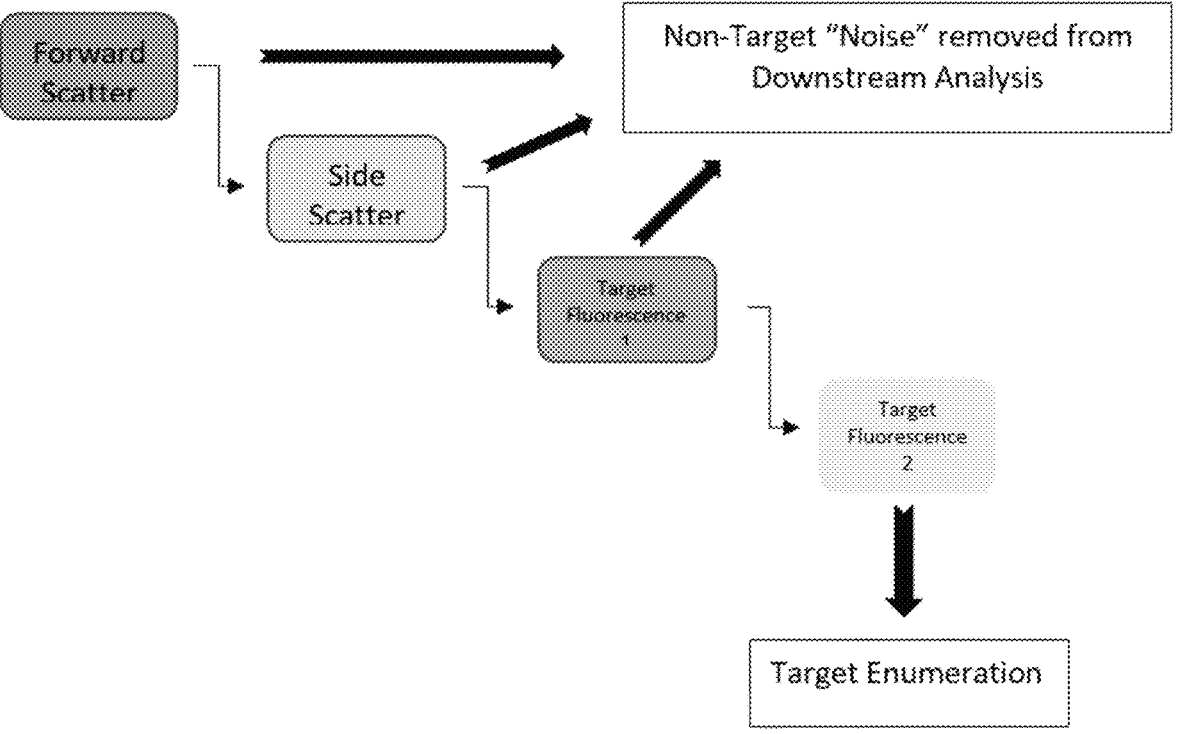
FIG. 1 shows an embodiment of the methods for detecting target microparticles.

In the description that follows, a number of terms are used extensively, and the following definitions are provided to facilitate understanding of various aspects of the invention. Use of examples in the specification, including examples of terms, is for illustrative purposes only and is not intended to limit the scope and meaning of the embodiments of the invention herein. Numeric ranges are inclusive of the numbers defining the range, in the specification, the word "comprising" is used as an open-ended term, substantially equivalent to the phrase "including, but not limited to," and the word "comprises" has a corresponding meaning.

The term "about" when used in conjunction with a value, for example, about 300 mM, means a value reasonably close to the value, i.e., within the range of ±20%, or ±10%, or ±5% of the value. In particular, it would include the value itself.

As used herein, the terms "a", "an", and "the" can refer to one or more unless specifically noted otherwise.

The term "substantially the same" refers to the fact that a first value is almost identical to a second value, and the difference between the two values are insignificant for intended purposes, e.g., the difference between the two values is less than 20%, less than 10%, or less than 5% of the greater value of the two.

As used herein, the terms "bacteriophage" and "phage" include viruses such as mycobacteriophage, mycophage (such as for fungi), *Mycoplasma* phage, and any other term that refers to a virus that can invade living bacteria, fungi, *Mycoplasma*, protozoa, yeasts, and other microscopic living organisms and uses them to replicate itself.

As used herein, the term "functionalize" refers to the process of linking capture agent molecules to a bead.

As used herein, the terms "gate" and "gates" generally refer to one or more selection criteria for events detected by a flow cytometer. For instance, an event may pass through one or more gates and continue for possible counting after it meets the criteria of the gate(s). In more specific examples, a gate may be a predefined amount of side scatter intensity, a predefined amount of forward scatter intensity, and/or a predefined amount of light emitted in a fluorescence channel, such as FL-1, FL-2, FL-3 or FL-4.

As used herein, "gating," refers to use of gates (one-dimensional gates or two-dimensional gates) to exclude events detected and/or isolate events of interest utilizing the same detection protocols. Gating as used in practicing various embodiments of the present disclosure may provide beneficial reduction of noise events or events that are not of interest in a flow cytometer assay.

In this disclosure, a concentration range listed or described as being useful, suitable, or the like, indicates that any and every concentration within the range, including the end points, is to be considered as having been stated. For example, a range "from 30 nm to 300 nm" is to be read as including each and every possible number along the continuum between about 30 nm and about 300 nm.

2. Introduction

The methods and compositions disclosed herein can be used to detect the presence of a target microparticle in a test sample. The target microparticle is often of submicron size, which often appears near the "noise" signature of existing cytometers, even when utilizing ultra-clean sheath fluid. This renders detection of these microparticles particularly challenging. The methods of this disclosure use specific functionalized beads of pre-defined size to capture these microparticles, such that the functionalized beads will position the microparticles, when present, outside the range of "noise". A gate is determined based on the position of the functionalized beads and is applied to a test sample that has been contacted with the functionalized beads to assess secondary characteristics. Secondary characteristics used herein include but are not limited to features such as size, the presence of a biomarker, and nucleic acids or lipid components of the target microparticle. In the case of SARS-COV-2, such secondary characteristics may be the presence of RNA, which can be detected using an intercalating fluorescent dye, or the S glycoprotein on the surface of the virus. In addition, the adhesion of multiple viral particles to a single bead will serve as a signal amplification mechanism, allowing a significantly lower limit of detection. The methods thus can detect the presence of microparticle with high specificity and sensitivity. The flow cytometry analysis platform is also advantageous in that it allows assays to be performed in multiplex format to determine the presence of multiple microparticles.

In terms of detecting the viral infection, such as from SARS-COV-2, direct determination of viral presence using orthogonal assessment available from flow cytometric analysis is an effective means to screen for COVID-19. Potential advantages of this direct assessment approach include higher clinical sensitivity and specificity, reducing susceptibility to any inhibitors present in the sample which can hinder the reverse transcriptase process, and lowering overall susceptibility to minor mutations of the viral nucleic acid (e.g., viral RNA). Additionally, this approach could offer a simple, rapid multiplex approach to identify different viral etiologies, for example, differentiating SARS-COV-2 from other viral etiologies, such as but not limited to, influenza A/B, by incorporating functionalized beads with different scatter and/or fluorescent characteristics as well as functionalization targets into the assay.

3. Target Microparticles

The methods disclosed herein can be used to detect a variety of target microparticles. Non-limiting examples of the microparticles include microorganisms as well as components thereof, e.g., an exosome, a microvesicle, a mini-cell, a virus (also referred to as a viral particle in this disclosure), a bacterium and antibodies. In some embodiments, the microparticle is a SARS-CoV-2 virus, an Ebola virus, or a Zika virus, or a part of any of the aforementioned viruses. The SARS-COV-2 virus comprises an RNA genome, which is surrounded by a protective coat. One of the proteins present on the coat is the S glycoprotein, which mediates entry into host cells.

4. Samples

The method disclosed herein can be used to identify samples that have been contaminated with the target microparticles. Samples containing target microparticles can be obtained from any suitable source. For example, the sample can be obtained from any organism of interest. Such organisms include, for example, plants and animals (e.g., mammals, including humans and non-human primates). In some cases, the sample can be obtained from cells, tissue, or polynucleotides of a population of such organisms of interest. As another example, the sample can be of a microbiome or microbiota. In some embodiments, the sample is obtained from a human. In some embodiments, the sample is an environmental sample, such as a sample of water, air, or soil.

Samples from an organism of interest (e.g., a human), may include, but are not limited to, samples of bodily fluids (including, but not limited to blood, urine, serum, lymph, saliva, anal and vaginal secretions, perspiration and semen); cells; tissue; biopsies, research samples (e.g., products of nucleic acid amplification reactions, such as PCR amplification reactions); purified samples, such as purified genomic DNA; RNA preparations; and raw samples (bacteria, virus, genomic DNA, etc.). In some cases, the sample is a throat swab sample, a nasal swab, or a sputum sample.

The concentrations of microparticles in the sample may vary, depending on the stage of the disease the patients are in and/or the manner the sample is collected. In some embodiments, the concentration of microparticles in the sample may range from 600 particles/ml to 1.5e11 particles/ml, e.g., from 10e2 particles/ml to 10e7 particles/ml, from 10e3 particles/ml to 10e6 particles/ml, from 10e3 to 10e5 particles/ml, or about 10e5 particles/ml.

5. Beads

The beads used in the method may take any shape. In the present disclosure, the size of the beads are represented by diameter, but this does not mean that the beads are necessarily spheres. The beads can be made of any materials, which include but not limited to latex, glass, ceramic, silica, metal, elastomer (e.g., silicone), paramagnetic, polystyrene, or polyacrylamide. In one embodiment, the beads are polystyrene beads. In some embodiments, the beads are magnetic. In some embodiments, the beads are not magnetic beads.

In some embodiments, the beads have a diameter that ranges from 10 nm to 10 µm, or 200 nm to 10 µm, e.g., from 400 nm to 8 µm, from 600 nm to 5 µm or from 1 µm to 5 µm.

In some embodiments, the beads used in the methods are carboxyl-functionalized and/or amino-functionalized so that they can be covalently linked to a capture agent of interest, as described below. In some embodiments, a portion of beads are amino-functionalized and a portion of the beads are carboxyl-functionalized. The term "carboxyl-functionalized," when referring to a bead, indicates that the bead comprises carboxyl groups, which can react with amino groups from other molecules (e.g., the capture agent molecules) to form covalent bonds. The term "amino-functionalized" indicates that the bead comprises amino groups, which can react with carboxyl groups from other molecules.

In some embodiments, the beads do not emit a detectable signal. However, the beads may emit certain background signal when analyzed on a fluorescence channel of a flow cytometer. The signals are typically referred to as autofluorescence, which can interfere with detection of the target microparticles. This negative interference can be reduced or eliminated by proper calibration of the cytometer before running the test sample. Auto-fluorescence can also be used as a measurement to further distinguish capture beads from particles with similar signals in other channels.

In some embodiments, the bead can emit a detectable signal, and such a bead is referred to as bead beacon. In some embodiments, the bead itself does not produce a detectable signal, but can bind to a secondary reagent that emits a detectable signal, as described below.

In some embodiments, the functionalized beads are present in a form of a solution in a concentration that ranges from about 10 to about 1,000 beads per μl

6. Capture Agents

The beads may be coated with molecules of one or more capture agents. Each capture agent disclosed herein is capable of binding specifically to a target microparticle. The types of capture agents that can be used to capture the target microparticle to the beads can vary widely. Non-limiting examples of capture agents include polypeptides, antibodies or binding portions thereof (e.g., Fab fragments), nucleic acids, aptamers, or phage.

The capture agent may specifically bind to a component (e.g., a surface protein) of the microparticle. In some embodiments, the target microparticle is a SARS-COV-2 virus, and the capture agent coated on the beads can specifically bind to the S protein on the SARS-COV-2 virus. In some embodiments, the capture agent is an ACE-2 receptor or a homolog thereof. For the purpose of this disclosure, an ACE-2 homolog is one that shares at least 95%, at least 90%, at least 85% or at least 80% sequence identity with the full protein of the human ACE-2 receptor. An ACE-2 homolog retains substantially the same binding affinity to the SARS-COV-2 virus as the human ACE-2 receptor.

In some embodiments, the capture agent binds to the target microparticle with high affinity. The Kd of the binding may range from 0.1 to 1000 nanomolar, or from 1000 nanomolar to 500 micromolar.

Capture agents can also be obtained by screening a combinatorial peptide library or small molecule compound library to identify candidates exhibiting specific binding affinity to the target microparticle. Illustrative examples include xenoproteins, as described in Gates et al., PNAS Jun. 5, 2018 115 (23) E5298-E5306, the entire content of which is herein incorporated by reference.

In some cases, the bead is functionalized with molecules of the same capture agent, where at least some of these molecules bind to the target microparticles. In some cases, the bead is coated with molecules of two or more different capture agents, each capture agent capable of binding to a different type or variant of the same targeted microparticle. Beads functionalized with different types of capture agents can be used in multiplex assays for detection of a variety of target microparticles using a variety of secondary reagents.

Figure 2:
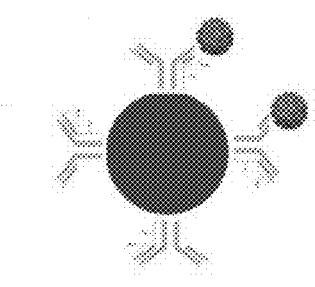
FIG. 2 illustrates embodiments of the methods where a bead is functionalized with capture agent molecules.
Figure 2:
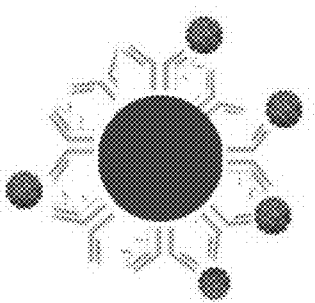
Figure 3A:
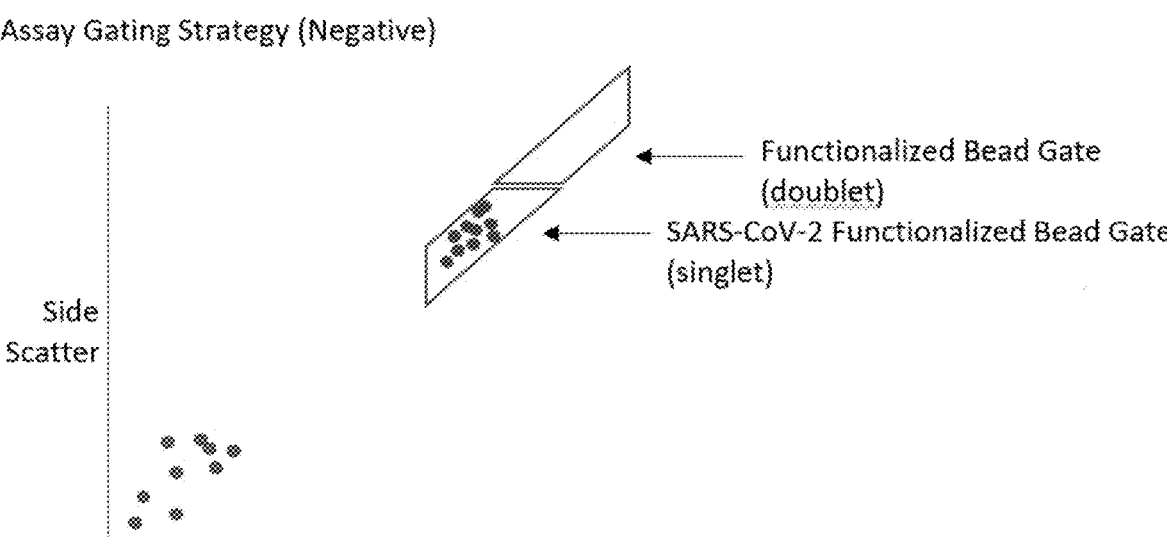
FIGS. 3A-D illustrate a gating strategy to identify the threshold that is used to determine the presence of microparticle in the sample.
Figure 3B:
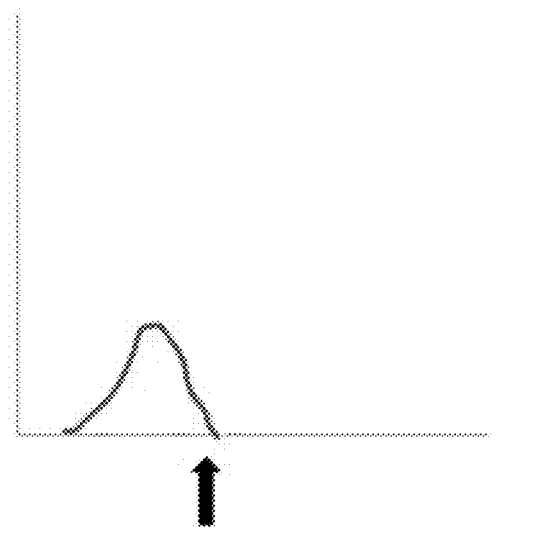
Figure 3C:
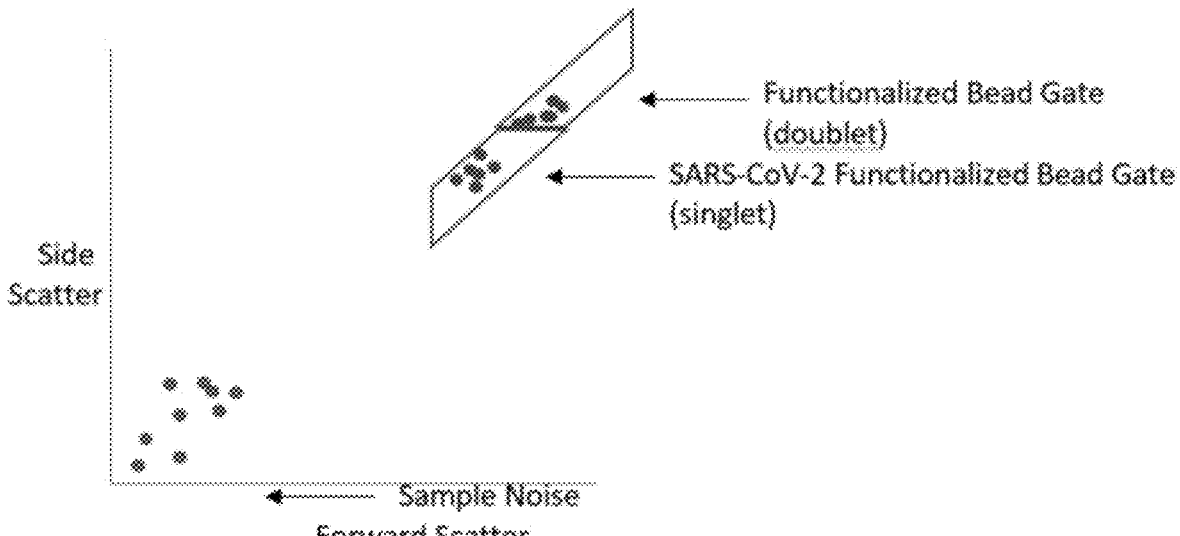
Figure 3D:
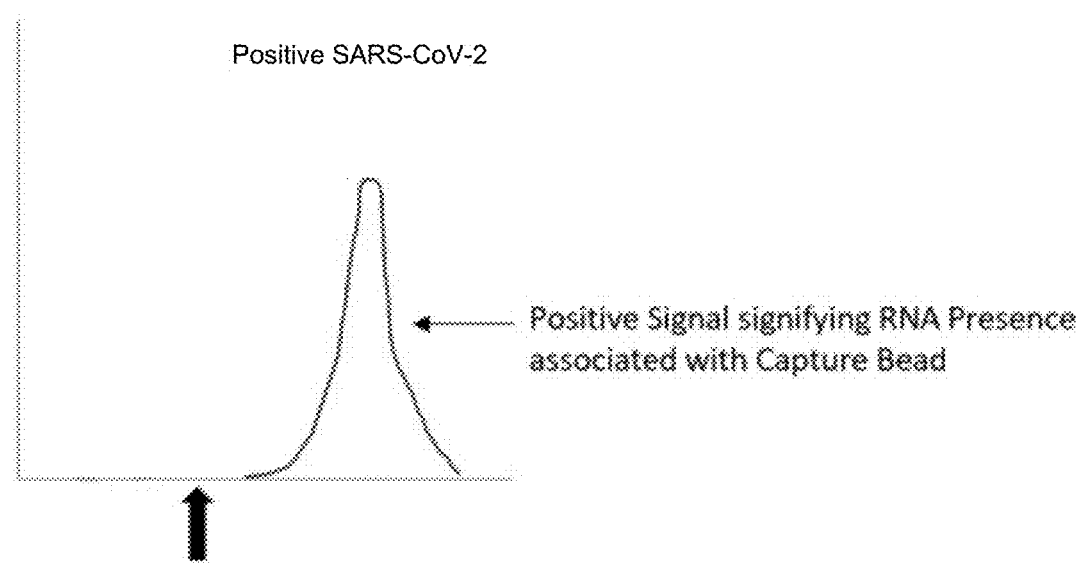

The number of the capture agent molecules immobilized on each functionalized bead may vary and may affect the efficiency of capturing the target microparticles. On the one hand, increasing the amount of capture agent molecules on each bead may attract a higher amount of microparticles, which can increase detection signal (see FIG. 2); on the other hand, increasing the amount of capture agent molecules per bead could cause steric hindrance and interfere with the binding between the capture agent molecules and the target microparticles. Thus, it is desirable to maintain the density of the capture agent molecules within an optimal range. For purposes of this disclosure, the term "density" refers to the percentage of the surface area of the bead that is covered by the capture agent molecules. A 100% density indicates that the entire surface of the bead is covered with capture agent molecules. The number of capture agent molecules required to reach 100% density can be determined by methods known to one of skill in the art, for example, by measuring signals resulted from binding of the beads to a serially diluted capture agent solutions. The capture agent molecules may be conjugated to a detectable signal such that the binding of the capture agent molecules to the beads can be quantified. The intensity of the signal may initially increase with the increasing number of capture agent molecules on the bead and then decreases. The number of capture agent molecules that corresponds to the maximum signal is the number of capture agent molecule that is required to reach 100% density. In some embodiments the density of the capture agent molecules on the functionalized beads ranges from about 1% to about 100%, e.g., from about 5% to about 80%, from about 10% to about 70% or from about 15% to about 60%. In one particular embodiment, the capture agent is a synthetic xenoprotein as described in Zhang et al. and the average density of the capture agent molecules per bead is about 10% to about 100%. In some embodiments, the number may vary from 1 to 10,000 capture agent molecules per bead, e.g., from 10 to 8,000, from 100 to 7,000, or from 1000 to 5000.

7. Producing Functionalized Beads

In some embodiments, the capture agent is covalently linked to the bead. In some embodiments, the capture agent is coupled to the beads through a linker. The term "linker" is used to refer to groups or bonds that normally are formed as the result of a chemical reaction and typically are covalent linkages. In some embodiments, the linker comprises a carboxyl group or an amino group, which forms covalent bonds with an amino group or a carboxyl group, respectively, on the capture agent molecules.

In some embodiments, the capture agent is non-covalently linked to the bead. In some embodiments, the capture agent comprises a biotin group and the bead comprises a streptavidin group, or vice versa; and the capture agent non-covalently couples with the bead through the interaction between streptavidin and biotin.

A linker used in this disclosure can be any linker apparent to those of skill in the art. Useful linkers may include, but are not limited to, alkylene, substituted alkylene, heteroalkylene, substituted heteroalkylene, arylene, substituted arylene, heteroarylene, and substituted heteroarylene. In certain embodiments, the linker is C1-10 alkylene or C1-10 heteroalkylene. In some embodiments, the linker is a polyethylene glycol (PEG) linker. Methods for immobilizing ligands through linkers to beads are well known in the art, and kits and reagents that can be used for this purpose are also commercially available.

8. Secondary Reagent

A secondary reagent used in the methods disclosed herein can be any molecule that can bind to the target microparticle, provided that said binding is capable of producing a detectable signal in a detection channel of the flow cytometer. In some embodiments, the secondary reagent comprises or is tagged with a detectable marker, e.g., a fluorophore, as further described below. Other detectable markers/labels include various enzymes, prosthetic groups, fluorescent materials, luminescent materials, bioluminescent materials, and radioactive materials. Examples of suitable enzymes include horseradish peroxidase, alkaline phosphatase, beta-galactosidase, or acetylcholinesterase. Examples of suitable prosthetic group complexes include streptavidin/biotin and avidin/biotin. Examples of suitable fluorescent materials include umbelliferone, fluorescein, fluorescein isothiocyanate, rhodamine, dichlorot[pi]azinylamine fluorescein, dansyl chloride or phycoerythrin. An example of a luminescent material includes luminol. Examples of bioluminescent materials include luciferase, luciferin, and aequorin.

In some embodiments, the secondary reagent binds to the target microparticle (e.g., a viral particle) in a nonspecific manner. This is to say, the secondary reagent is capable of binding to any kind of target microparticles that are attached to the functionalized beads. For example, the secondary reagent can permeate the membrane or protective coat of the microparticle and intercalate with the nuclei acid of any microorganism. In one embodiment, the secondary reagent is an RNA dye, which is capable of binding to the RNA of a viral particle (e.g., SARS-COV-2). Non-limiting examples of secondary reagents that can bind to nucleic acids in a non-discriminatory manner include Acridine Orange. Acridine Orange has an excitation wavelength of about 488 nm and an emission wavelength of about 530 nm, which can be detected in a fluorescence channel of the cytometer. In another embodiment, the secondary reagent can bind to a lipid component of any organism. In one embodiment, the secondary reagent is a lipophilic carbocyanine dye. Non-limiting examples of the lipophilic dye include DiO (available from ThermoFisher Scientific, Waltham, MA).

In some embodiments, the secondary reagent specifically binds to the target microparticle. For example, the secondary reagent can be an antibody or a Fab fragment that binds to an epitope of the microparticle specifically. In some embodiments, the secondary reagent does not compete with the capture agent on the functionalized beads in binding to the target microparticle, i.e., the secondary reagent and the capture agent bind to two different components of the target microparticle.

As described above, a secondary reagent may comprise a fluorophore. A fluorophore is a chemical compound that absorbs light energy at one wavelength and nearly instantaneously emits light at another, longer wavelength of lower energy. Most fluorophores are either heterolytic or polyaromatic hydrocarbons. The fluorescence signature of each fluorophore is unique in that it provides the wavelengths and amount of light absorbed and emitted. During fluorescence, the absorption of light excites electrons to a higher electronic state where they remain for about $1\text{-}10 \times 10^{-8}$ seconds, and then they return to the ground state by emitting a photon of energy. When a population of fluorophores is excited by light of an appropriate wavelength, fluorescent light is emitted. The light intensity can be measured by e.g., a flow cytometer or a fluorimeter.

Fluorescence intensity depends on the efficiency with which fluorophores absorb and emit photons, and their ability to undergo repeated excitation/emission cycles. The intensity of the emitted fluorescent light is a linear function of the amount of fluorophores present. The signal becomes nonlinear at very high fluorophore concentrations.

A wide variety of fluorophores can be used in the oligonucleotide probe, including but not limited to: CAL Fluor® Gold 540, CAL Fluor® Orange 560, Quasar® 670, Quasar® 705, 5-FAM (also called 5-carboxyfluorescein; also called Spiro (isobenzofuran-1 (3H), 9'-(9H) xanthene)-5-carboxylic acid-3'6'-dihydroxy-3-oxo-6-carboxyfluorescein); 5-Hexachloro-Fluorescein ([4,7,2',4',5',7'-hexachloro-(3',6'-dipivaloyl-fluoresceinyl)-6-carboxylic acid]); 6-Hexachloro-Fluorescein ([4,7,2',4',5',7'-hexachloro-(3',6'-dipivaloylfluoresceinyl)-5-carboxylic acid]); 5-Tetrachloro-Fluorescein ([4,7,2',7'-tetra-chloro-(3',6'-dipivaloylfluoresceinyl)-5-carboxylic acid]); 6-Tetrachloro-Fluorescein ([4,7,2',7'-tetrachloro-(3',6'-dipivaloylfluoresceinyl)-6-carboxylic acid]); 5-TAMRA (5-carboxytetramethylrhodamine; Xanthylium, 9-(2,4-dicarboxyphenyl)-3,6-bis (dimethyl-amino); 6-TAMRA (6-carboxytetramethylrhodamine; Xanthylium, 9-(2,5-dicarboxyphenyl)-3,6-bis(dimethylamino); EDANS (5-((2-aminoethyl) amino)naphthalene-1-sulfonic acid); 1,5-IAEDANS (5-((((2-iodoacetyl)amino)ethyl) amino) naphthalene-1-sulfonic acid); DABCYL (4-((4-(dimethylamino)phenyl) azo)benzoic acid) Cy5 (Indodicarbocyanine-5) Cy3 (Indo-dicarbocyanine-3); and BODIPY FL (2,6-dibromo-4,4-difluoro-5,7-dimethyl-4-bora-3a,4a-diaza-s-indacene-3-propionic acid), Rox, as well as suitable derivatives thereof.

9. Quencher

The quencher (also referred to as the quencher moiety) used in the present disclosure can be any material that can quench detectable signal, e.g., emission of fluorescence. In some embodiments, the quencher binds to the functionalized beads through binding to the one or more capture agents on the functionalized beads via a low affinity analog of the target moiety. This low affinity moiety may possess a protein-to-quencher ratio of 1:1. It may also have a protein-to-quencher ratio of 1:2, 1:3, 1:4, or 1:5. In these embodiments, the functionalized beads themselves can emit fluorescence, and the binding quenches the detectable signal from the functionalized beads.

The quencher binds to the functionalized beads with less affinity than the target microparticle does. For example, the Kd of the binding between the quencher and the functionalized beads is greater than the Kd of the binding between the microparticle and the functionalized beads. Therefore, when contacted with a sample comprising the target microparticle, the quencher is displaced by the target microparticle to permit the emission of the signal from the functionalized beads.

Quenching of the signal from the functionalized beads by the quencher may involve several alternative mechanisms. In some embodiments, quenching may involve a type of energy transfer, including but not limited to, a photoelectron transfer, a proton coupled electron transfer, dimer formation between closely situated fluorophores, transient excited state interactions, collisional quenching, or formation of non-fluorescent ground state species. For example, a quencher may be joined with a fluorophore on the functionalized beads (e.g., on the beads themselves or the capture agent molecules immobilized on the beads) in a configuration that permits energy transfer from the fluorophore to the quencher to result in a reduction of the fluorescence by Fluorescence Resonance Energy Transfer (FRET).

The quencher used in the invention may or may not emit fluorescence itself upon energy transfer from the fluorophore. Some quencher moieties, for example, tetramethyl-6-carboxyrhodamine (TAMRA), can re-emit the energy absorbed from the fluorophore at a wavelength or using a signal type that is also detectable but distinguishable from the fluorophore emission. Other quencher moieties, such as the Black Hole Quenchers (BHQs), including Black Hole Quencher-1 (BHQ-1), Black Hole Quencher-2 (BHQ-2), and Black Hole Quencher-3 (BHQ-3), have no native fluorescence and thus can virtually eliminate background problems seen with other quencher moieties. The Black Hole Quenchers, which can be used to quench almost all fluorophores, are commercially available, for example, from Biosearch Technologies, Inc. (Novato, CA). Additional quencher moieties include but are not limited to DABCYL and rhodamine dyes, such as tetrapropano-6-carboxyrhodamine (ROX).

The degree of the reduction of fluorescence of a fluorophore by the quencher (referred to herein as "quenching" or "quenched") is not limited, per se, except that a quenching effect should minimally be detectable by whatever detection instrumentation is used. Fluorescence is "quenched" when the fluorescence emitted by the fluorophore is reduced as compared with the fluorescence in the absence of the quencher by at least 10%, for example, 15%, 20%, 30%, 40%, 50%, 60%, 70%, 80%, 90%, 95%, 98%, 99%, 99.9% or more.

10. Methods

This disclosure provides methods of detecting a target microparticle in a test sample. Sample collection is typically performed by using a swab on the patient's nasal or throat membranes or collecting any body fluids, aspiration fluid or tissues that may have been exposed to the target microparticle. The samples are typically immersed in a suitable media, which maintains the integrity of the virus. Non-limiting examples of this transportation media include Viral Transport Media (which may include e.g., FBS, gentamicin, and/or amphotericin). Suitable transportation media are also commercially available, for example, from Becton Dickinson (Franklin Lakes, NJ). In some embodiments, the patient samples are concentrated, diluted or treated through other means to render the target microparticles in a concentration more suitable for testing. Wash buffer, such as Phosphate Buffered Saline, may also be used in one or more steps in preparing the sample for testing.

A test sample prepared as described above can be mixed with the functionalized beads. The functionalized beads may be present in appropriate concentrations that are sufficient to capture the target microparticles in the test sample. In some embodiments, the molar ratio of the target microparticle to the functionalized beads ranges from 10e6 to 1, e.g., from 10e5 to 1, from 10e4 to 1, or from 10e3 to 1, or 10e2 to 1. In some embodiments, the functionalized beads and other necessary reagents are preloaded on a cartridge, and the test sample is added to the preloaded cartridge. In some embodiments, the functionalized beads and other necessary reagents are added to a cartridge by the system, where the sample is pre-loaded.

The test sample may be treated in a number of preanalytical steps such as incubation with the functionalized beads (e.g., on the cartridge) for a period of time to ensure efficient capture of the target microparticles in the test sample. The manner of the treatment and the length of the incubation period may vary. In some embodiments, the incubation period may last about 1 to about 60 minutes, e.g., from about 5 minutes to about 50 minutes, from about 10 minutes to about 40 minutes, or about 15 minutes.

In some embodiments, a secondary reagent is added to the mixture. The secondary reagent can bind to the target microparticle that have been captured on the functionalized beads and produce a detectable signal.

In some embodiments, the functionalized beads can emit fluorescence through the beads. In some embodiments, the functionalized beads can emit fluorescence through the capture agent molecules. In these embodiments, a quencher that has less affinity to the functionalized beads than the target microparticles is also used. In the absence of the target microparticle, the quencher binds to the functionalized beads through binding to the capture agents and quenches the fluorescence. In the presence of the target microparticles, the target microparticle would displace the quencher from the capture agent to permit the detection of the fluorescence from the functionalized beads.

Figure 4:
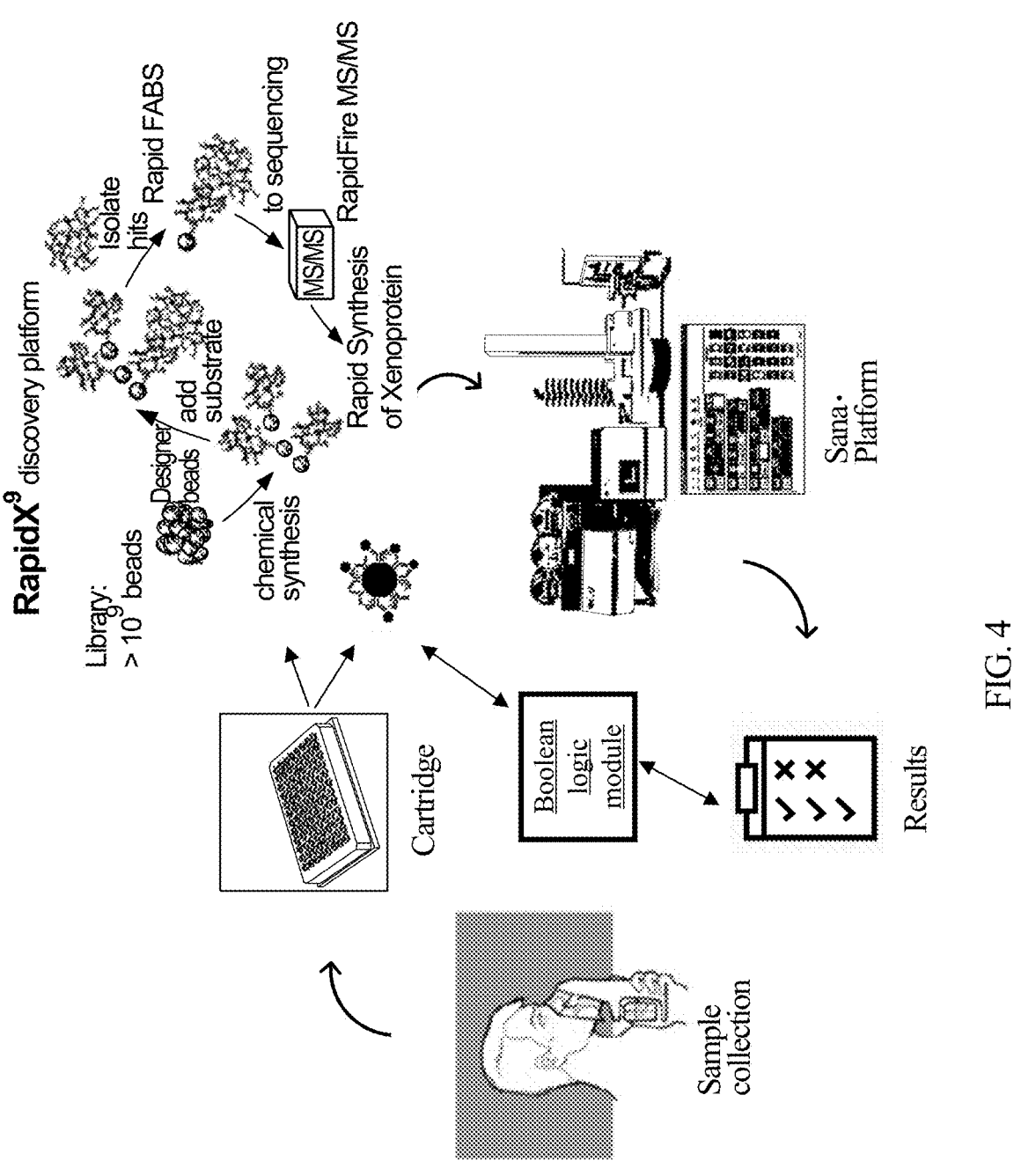
FIG. 4 illustrates various embodiments using the methods disclosed herein to detect the presence of a target microparticle in a patient. A Boolean logic module is used to optimize the assay conditions in the case the result is equivocal.

An exemplary workflow from collecting test samples to detecting the presence of target microparticles in the test samples is illustrated in FIG. 4.
Flow Cytometry Gating Signals from the second reagent or the functionalized beads are detected by a fluorescence channel of the flow cytometer. As described above, the small size of the target microparticles poses a particular challenge for direct detection using flow cytometry. These microparticles often appear indistinguishable from noise of the cytometer and thus undetectable. The methods disclosed in this application use beads having an average size within a suitable range as disclosed to capture the microparticles to form target microparticle-loaded beads, which are of sufficient size and can be clearly differentiated from instrumental noise using scatter, fluorescence, auto fluorescence, time of flight.

The method includes first analyzing a calibration sample using the flow cytometer. The calibration sample comprises the functionalized beads and the other necessary reagent for developing fluorescence for detection, such as a secondary reagent. In other words, the calibration sample comprises the same components except for the test sample comprising the target microparticle. A gate is selected based on a scatter (e.g., the forward scatter and/or a side scatter) of the calibration sample, and the gate includes only functionalized beads and excludes other particles. Selecting the optimal size, composition and chemistry of the beads would advantageously allow the exclusion of particles that are outside the isolation gate of the target microparticle loaded beads, thus reducing the non-specific signals. Particles that are outside the isolation gate include cells that may producer larger or smaller signals, e.g., including mammalian cells or bacteria cells, or debris. This gate is applied to the signal associated with a secondary characteristic of the target microparticle, e.g., the presence of the viral RNA. A threshold that is equal to or greater than the maximum signal of the secondary characteristics is determined. This maximum signal often represents the auto-fluorescence from the beads, or in the case where the functionalized beads emit fluorescence themselves (in the absence of the secondary reagent), this maximum signal represents the residual fluorescence emitted by the beads after being quenched by the quencher.

A test sample is then analyzed on the same flow cytometer. A secondary characteristic is assessed by measuring signal from the corresponding fluorescence channel, which is subjected to the gate. If the signal is sufficiently greater than a threshold (e.g., as disclosed above), the test sample is determined to comprise the target microparticle. The term "sufficiently greater" indicates that the signal from the test sample (e.g., the mean fluorescence intensity) is at least 5%, at least 10%, at least 20%, or at least 50% higher than a predetermined threshold or the signal from a control sample. If the signal is sufficiently lower than the threshold, the sample may be subjected to a retesting using further optimized parameters relating to the functionalized beads and assay condition, as described below.

The claimed methods that employ the functionalized beads can detect target microparticles with superior sensitivity and efficiency. For example, viral particles can be detected with a detection limit of about 10 to 10e9 particles per ml, e.g., 10 to 10e3 particles per ml, or about 100 to 10e3 particles per ml. The time it takes to complete the detection, from contacting the sample with functionalized beads to detection of the target microparticles in the test sample, may take less than 5 hours, e.g., less than 2 hours, less than 1 hour, less than 30 min, or less than 20 min. In some embodiments, the method can be performed within about 15 min.

In some embodiments, the target microparticle loaded beads are sorted on the cytometer and are collected. These collected target microparticles can be further analyzed by downstream assays as needed, for example, sequencing.

Figure 5:
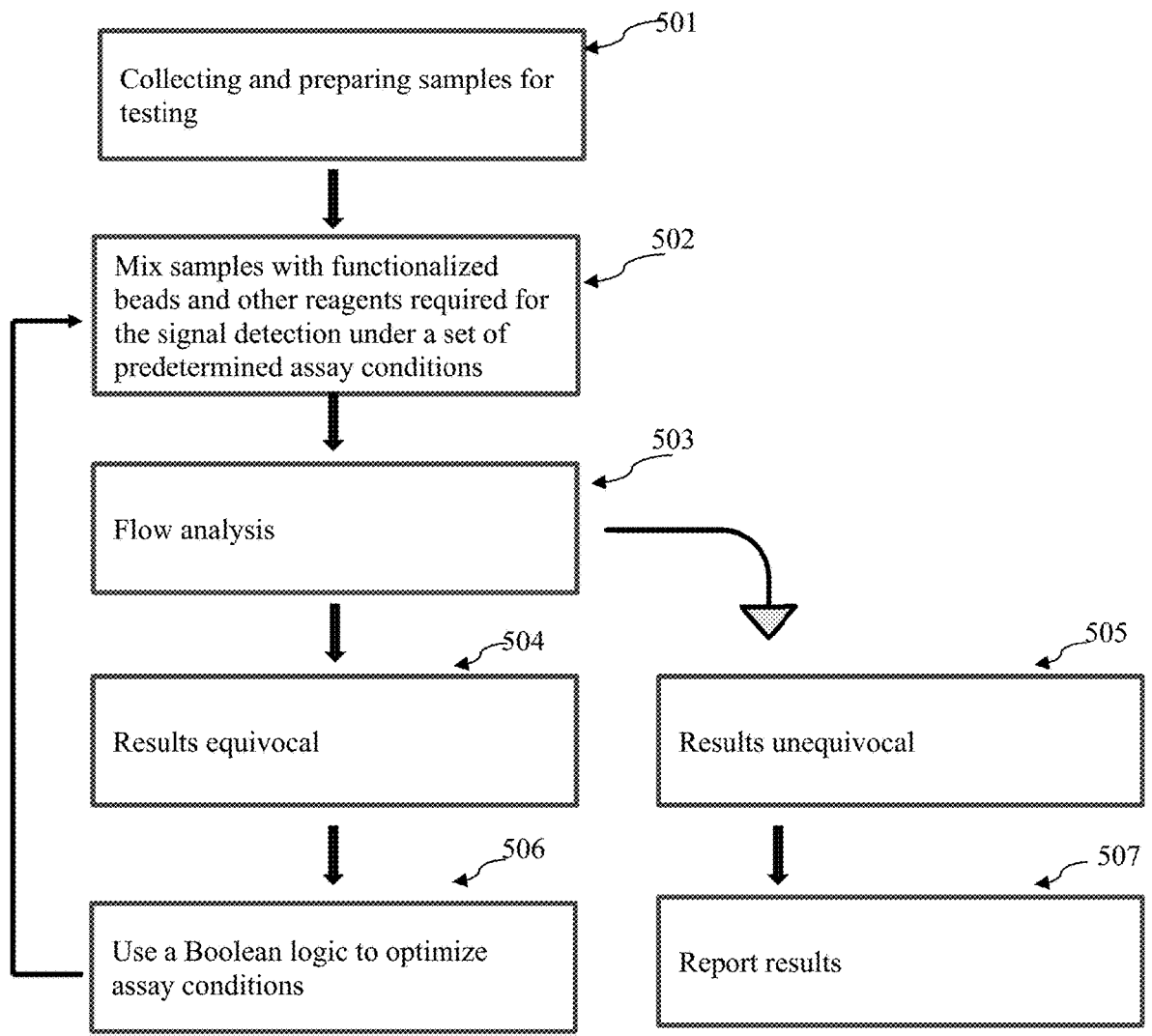
FIG. 5 illustrates an exemplary work flow of using the methods disclosed herein to detect the presence of a target microparticle in a patient.

In some embodiments, the method is performed using a system (e.g., the Shero Diagnostics platform) that employs a fully automated, robotic architecture, with easy user programming interface and Boolean logic. Exemplary embodiments of these embodiments are disclosed in U.S. Pat. No. 10,338,897, the entire content of which is herein incorporated by reference. The system is capable of generating reproducible data and performing assay optimization in real time. For example, the system can perform an initial analysis based on scatter and/or fluorescence signals, and then use a Boolean logic to automatically adjust and optimize the concentration the functionalized beads, the concentration of microparticles in the test sample, and/or the concentration of the secondary reagent. An illustration of this embodiment is shown in FIG. 5. In one embodiment, functionalization of the beads with the capture agent will occur at multiple protein levels to optimize capture through a dilution series of spiked target microparticles (e.g., the SARS-COV-2 viral particles). Binding of viral particles is expected to have a combination of effects: potential reduction in expected bead enumeration in a pre-defined gate by bead agglutination and a change in scatter, auto-fluorescence and fluorescence characteristics due the presence of one or more viral particles per bead. Additionally, optimization of a secondary reagent (e.g., the fluorescence lipid-specific dye) will be determined to improve assay specificity. Fluorescence signal may be elucidated from the bead singlet, doublet, and triplet gates taking into account the potential of bead agglutination.

Multiplexing

The methods disclosed herein can also be used to detect more than one type of microparticles in a test sample or in a plurality of samples. This feature, referred to as multiplexing, can be very useful for testing in a clinical setting. The beads can be functionalized with more than one capture agent, each recognizing a different type of target microparticles. For example, one capture agent may recognize SARS-COV-2, another may recognize an influenza, and yet another may recognize an Ebola virus. In some embodiments, each bead may comprise two or more different capture agents. In some embodiments, each bead may comprise only one capture agent and beads of varying characteristics such as size, composition, surface roughness or chemistry having different capture agents are mixed to form a mixture of beads, which are then used to assess the test sample in a multiplex assay.

In some embodiments, the multiplexing assay identifies different viral etiologies, for example, differentiating SARS-COV-2 from other viral etiologies, such as but not limited to influenza A/B, by incorporating functionalized beads with different light scatter characteristics into the assay.

In some embodiments, the different capture agents used in the multiplexing assay emit fluorescence that can be distinguished by the flow cytometer. For example, they may have different excitation wavelength/emission profile, and their fluorescence can be detected in different fluorescence channels of the flow cytometer.

In some embodiments, a multiplex assay can be performed to analyze a plurality of samples in one single mixture, using functionalized beads that have unique identification characteristics. As used herein, the term "unique identification characteristics," with regard to functionalized beads, indicates that functionalized beads that are used to contact any one of the plurality of samples are distinguishable from functionalized beads that are used to contact any other sample of the plurality of samples. The characteristics that can be used to distinguish the functionalized beads that contact different samples are referred to as unique identification characteristics. In some embodiments, the unique identification characteristics include, but are not limited to, the size of the beads, the fluorescence characteristics (e.g., autofluorescence) of the beads, or both. The fluorescence characteristics include, but are not limited to, excitation/emission wavelength and intensity. In some cases, one or more of the unique characteristics can be detected by flow cytometry. For example, the size of the beads can be detected and beads having different sizes can be distinguished using size scatter and/or forward scatter, and fluorescence characteristics of the beads can be detected and beads having different fluorescence characteristics can be distinguished using the fluorescence channels.

In some cases, each sample is from a different patient, and the plurality of samples are obtained from multiple patients. In some cases, the multiplex assay comprises contacting a plurality of patient samples with a plurality of functionalized beads having unique identification characteristics, such that each sample can be uniquely identified by the detection of the unique identification characteristics. The functionalized beads used in the assay are coated with molecules of a capture agent recognizing the target microparticle and added to individual samples prior to sample pooling. Samples that have been contacted with the functionalized beads may be combined in one single mixture, which are then subjected to flow cytometry analysis. A positive signal associated with the binding of the functionalized beads to the target microparticles can be traced to a particular sample based on the detected signal indicating the unique identification characteristics of the beads.

11. Evaluating Effectiveness of the Blocking Agents

The methods provided in this disclosure can also be used to assess whether a candidate blocking agent can block the binding of the target microparticle (e.g., a virus, such as SARS-CoV-2) to its cognate receptor. The capture agent that is coated on the bead can be a receptor that can specifically bind to the target microparticle ("cognate receptor"). A secondary reagent is added to detect the binding between the target microparticle and its cognate receptor. A first reaction is set up by mixing a first aliquot of the test sample with the functionalized beads in the presence of the candidate blocking agent and the secondary agent. In parallel, a second reaction is set up by mixing a second aliquot of the test sample with the functionalized beads and secondary reagent in the absence of the candidate blocking agent. Signals from the first reaction and the second reaction are measured and compared; if the signal from the first reaction is less than the signal from the second reaction, the candidate blocking reagent is determined to be able to block the binding between the microparticle and its cognate receptor. The blocking capability of the blocking agent can be reflected by the difference between the first and second signals. For example, a blocking reagent may result in a signal decrease of at least 20%, at least 30%, at least 40%, or at least 50% as compared to the control sample. Blocking agents identified using the methods disclosed herein can be further evaluated for therapeutic effect in other assays, for example, in vitro and in vivo efficacy studies.

12. Kits

In some embodiments, the disclosure provides a kit for detecting a target microparticle in a test sample. The kit may comprise a plurality of functionalized beads, each linked to one or more capture agent molecules. These capture agent molecules are capable of binding to the target microparticle specifically.

In some embodiments, the kit further comprises a secondary reagent, wherein the secondary reagent is capable of binding to the target microparticle, and said binding produces a detectable signal in a detection channel of a flow cytometer.

In some embodiments, the functionalized beads are capable of emitting fluorescence, and the kit further comprises a quencher. The quencher is capable of binding to the functionalized beads through binding to the capture agents on the functionalized beads, thus reducing or eliminating the bead fluorescence.

In some embodiments, the kit may further comprise one or more reagents selected from the group consisting of wash buffers, buffers for making dilutions of the test samples, buffers for permeabilizing microparticles. The kit may also comprise the storage or transportation media, which is configured to maintain the affinity of the target microparticle to the functionalized beads.

13. Systems

In some aspects, a system is used to detect the presence of a target microparticle. The system may comprise a cytometer and a cartridge for loading the samples. The cartridge can be inserted into the cytometer for analysis. In some embodiments, the cartridge is preloaded with some or all of the requisite reagents, including, e.g., functionalized beads and/or the secondary reagents (e.g., the RNA intercalating dye).

The system uses a flow cytometer to characterize and distinguish the target microparticle loaded beads from unloaded beads (i.e., beads that are not loaded with target microparticles). Various flow cytometers that can be used for the analysis are commercially available. In one embodiment, the flow cytometer is the Shero Diagnostics Automated Sana platform.

In some embodiments, the system further comprises a component for collecting samples from the patients. For example, the system may comprise containers for a surfactant, or a washing agent, and a media for transporting the test samples comprising the target microparticles. The system may also comprise components that are configured for transporting the test sample in suitable media to maintain the affinity of the target microparticle to the functionalized beads.

In some embodiments, the system is a fully automated, high-throughput cell analysis platform that is suitable for clinical diagnostics. For example, the system may comprise components that are configured to perform sample preparation steps, such as dilutions, concentrations, centrifugation, incubation, permeabilization. One such example is the Shero Diagnostics Automated Sana platform, which has a robust dynamic range and ultra-sensitive fluorescence detection capabilities. The system allows for determination of cells/particles in the single micron/sub-micron range and further characterizations based on orthogonal assessment of viral-specific parameters. The term "orthogonal assessment" refers to the strategy of using gates to exclude certain events for downstream characterization. In some embodiments, the system may further comprise components configured for robust data collection and analysis during the assay optimization process, which allows for a rapid application of assay-specific software for IVD assay optimization and commercialization for clinical entities.

Diagnostic methods and systems disclosed herein offer superior specificity and sensitivity and multiplexing capability in detecting a variety of target microparticles. These are important for making precision medicine a reality and protecting our society from the potential harm resulting from erroneous social policy instituted based on incorrect or insufficient data.

14. References

Zhang, N. et al. Recent advances in the detection of respiratory virus infection in humans; *J Med Virol.* 2020 April; 92 (4): 408-417

Wang, C., et al. A novel coronavirus outbreak of global health concern. Lancet; 2020 Feb. 15; 395 (10223): 470-473

Huang, C. et al. Clinical features of patients infected with 2019 novel coronavirus in Wuhan, China. Lancet; 2020 Feb. 15; 395 (10223): 497-506

CDC: Interim Guidelines for Collecting, Handling, and Testing Clinical Specimens from Persons for Coronavirus Disease 2019 (COVID-19). www.cdc.gov/coronavirus/2019-nCoV/lab/guidelines-clinical-specimens.html Dong, L. et al. Highly accurate and sensitive diagnostic detection of SARS-COV-2 by digital PCR. www.medrxiv.org/content/10.1101/2020.03.14.20036129v2

Pan, Y. et al. Viral load of SARS-COV-2 in clinical samples; Lancet. 2020 Apr. 1; Volume 20 (4)

Zhang, G. et al. The first-in-class peptide binder to the SARS-COV-2 spike protein. bioRxiv. 2020

Lippe, R. Flow Virometry: A Powerful Tool to Functionally Characterize Viruses. *J Virol.* 2018 Feb. 1; 92 (3)

Zucker, R., Ortenzio, J., Boyes, W. Characterization, detection, and counting of metal nanoparticles using flow cytometry. Cytometry Vol 89 (2) 2015

Arakelyan, A. et al. Nanoparticle-based flow virometry for the analysis of individual virions. 2013. *J Clin Invest.* 2013; 123 (9): 3716-3727

Shang, J., Ye, G., Shi, K. et al. Structural basis of receptor recognition by SARS-COV-2. *Nature* (2020).

Meng, Y. et al. A highly conserved cryptic epitope in the receptor-binding domains of SARS-COV-2 and SARS-COV. *Science* 3 Apr. 2020:

Zou, L. et al. SARS-COV-2 Viral Load in Upper Respiratory Specimens of Infected Patients. NEJM 19, March 2020

It is understood that the examples and embodiments described herein are for illustrative purposes only and that various modifications or changes in light thereof will be suggested to persons skilled in the art and are to be included within the spirit and purview of this application and scope of the appended claims. All publications, sequence accession numbers, patents, and patent applications cited herein are hereby incorporated by reference in their entirety for all purposes.

EMBODIMENTS

This disclosure comprises the following, exemplary embodiments.

Embodiment 1. A method of detecting a target micropar-
ticle in a test sample, the method comprising: (a)
contacting the test sample containing the target
microparticle with a plurality of functionalized beads,
wherein the size of the target microparticle is less than
1 µm, wherein the functionalized beads comprise beads
coated with molecules of a capture agent, wherein at
least some molecules of the capture agent bind to the
target microparticle, thereby forming target micropar-
ticle-loaded beads comprising the functionalized beads
and the target microparticle; and (b) detecting the target
microparticle-loaded beads using a flow cytometer,
thereby detecting the presence of the target micropar-
ticle in the test sample, wherein the target micropar-
ticle-loaded beads are detected with a detection limit
that ranges from 10 microparticles per ml to 10e4
microparticles per ml.

Embodiment 2. The method of embodiment 1, wherein
the method further comprises contacting the test sample
with a secondary reagent before step (a), wherein the
secondary reagent binds to the microparticle and said
binding is capable of producing a detectable signal in a
detection channel of the flow cytometer.

Embodiment 3. The method of any one of embodiments
1-2, wherein the method further comprises after step (a)
but before (b), contacting the target microparticle-
loaded beads with a secondary reagent, wherein the
secondary reagent binds the microparticle, wherein the
binding produces a detectable signal in a detection
channel of the flow cytometer.

Embodiment 4. The method of embodiment 2, wherein
the secondary reagent specifically binds to a surface
component on the microparticle.

Embodiment 5. The method of embodiment 2, wherein
the secondary reagent and capture agents bind to dif-
ferent surface components on the microparticle.

Embodiment 6. The method of any one of embodiments
2-5, wherein the microparticle is a SARS-COV-2 viral
particle, wherein the viral particle comprises membrane
lipids and nucleic acids, and wherein the secondary
reagent intercalates to the nucleic acids or the lipids.

Embodiment 7. The method of any one of embodiments
2-6, wherein the secondary reagent is a member
selected from the group consisting of a cell-permeant,
an RNA-specific dye or a lipophilic carbocyanine dye.

Embodiment 8. The method of any one of embodiments
1-7, wherein the functionalized beads are capable of
emitting a detectable signal, wherein step (a) further
comprises adding a quencher to the test sample, and
wherein the quencher is capable of binding to the
functionalized beads in the absence of the target
microparticle, wherein binding quenches the detectable
signal from the functionalized beads.

Embodiment 9. The method of embodiment 8, wherein
the quencher binds to the functionalized beads with less
affinity than the target microparticle does.

Embodiment 10. The method of embodiment 8 or
embodiment 9, wherein the quencher binds to the
functionalized beads through binding to the capture
agents on the functionalized beads, thus reducing or
eliminating the bead fluorescence.

Embodiment 11. The method of any one of embodiments
8-10 where presence of the target microparticle in the
sample displaces the quencher from binding to the
functionalized beads.

Embodiment 12. The method of any one of embodiments
2-11, wherein detecting the target microparticle-loaded beads in the test sample comprises: (1) (i) analyzing a
calibration sample comprising functionalized beads
with or without the secondary reagent using the flow
cytometer, wherein the beads and functionalized beads
in the reference sample are of the same type as the
beads and functionalized beads used to analyze the test
sample in step (a), and wherein the calibration sample
does not comprise the target microparticle, (ii) collect-
ing signals from the scatter and/or fluorescence chan-
nels, (iii) determining relative positions of the func-
tionalized beads in a flow cytometry plot displaying the
scatter and/or fluorescence channels, and selecting at
least one gate that includes only functionalized beads
and excludes other particles, and (iv) determining a
threshold that is greater than the signal from the detec-
tion channel for the calibration sample based on the at
least one gate; (2) analyzing the test sample that has
contacted the functionalized beads using the flow
cytometer; and (3) detecting the signal generated from
the detection channel for the test sample that has
contacted the functionalized beads based on the at least
one gate, wherein the signal is sufficiently greater than
the threshold, thereby detecting the target micropar-
ticle.

Embodiment 13. The method of any one of embodiments
8-12, wherein detecting the target microparticle-loaded
beads in the test sample comprises: (1) (i) analyzing a
calibration sample comprising functionalized beads
and the quencher using the flow cytometer, wherein the
functionalized beads in the reference sample are of the
same type as the functionalized beads used to analyze
the test sample in step (a), and wherein the calibration
sample does not comprise the target microparticle, (ii)
collecting signals from the scatter and/or fluorescence
channels, (iii) determining relative positions of the
functionalized beads in a flow cytometry plot and
selecting a gate that includes the functionalized beads
and excludes other particles including but not limited to
cells and debris, and (iv) determining a threshold that
is greater than the signal from a detection channel from
the calibration sample based on the gate; (2) analyzing
the test sample that has contacted the functionalized
beads using the flow cytometer; and (3) detecting the
signal generated from the detection channel for the test
sample that has contacted the functionalized beads
based on the gate, wherein the signal is sufficiently
greater than the threshold, thereby detecting the target
microparticle.

Embodiment 14. The method of any one of embodiments
1-13, wherein the target microparticle is a member
selected from the group consisting of a virus, a viral
particle, a bacterium, a minicell, an exosome, and a
microvesicle.

Embodiment 15. The method of any one of embodiments
1-14, wherein the target microparticle is present in the
test sample in a concentration that ranges from about
10e1 to about 10e7 of the target microparticle per
milliliter.

Embodiment 16. The method of any one of embodiments
1-15, wherein the target microparticle is a SARS-
COV-2 virus or part thereof.

Embodiment 17. The method of embodiment 16, wherein
the capture agent binds to the S protein on the SARS-
COV-2 virus.

Embodiment 18. The method of any one of embodiments
1-17, wherein the bead is a latex bead.

Embodiment 19. The method of any one of embodiments 2-18, wherein the bead has a diameter of 10 nm to 10,000 nm.

Embodiment 20. The method of embodiment 19, wherein 1% to 100% of the surface of the beads is covered with the capture agents.

Embodiment 21. The method of embodiment 17, wherein the bead is capable of emitting auto-fluorescence.

Embodiment 22. The method of embodiment 19, wherein each bead is coated with 1-10e6 capture agent molecules.

Embodiment 23. The method of embodiment 19, wherein the bead is capable of emitting fluorescence.

Embodiment 24. The method of any one of embodiments 1-23, wherein the capture agent is a member selected from the group consisting of a polypeptide, an antibody or binding portion thereof, a nucleic acid, an aptamer, and a phage.

Embodiment 25. The method of any one of embodiments 1-24, wherein the capture agent is linked to the bead through non-covalent coupling.

Embodiment 26. The method of any one of embodiments 1-25, wherein the capture agent is covalently linked to the bead.

Embodiment 27. The method of embodiment 26, wherein the capture agent is covalently linked to the bead via a covalent bond formed between a carboxyl group and an amino group.

Embodiment 28. The method of any one of embodiments 1-27, wherein contacting the test sample with a functionalized bead comprises incubating the test sample with the functionalized bead for a period of time that ranges from about 1 to about 60 minutes.

Embodiment 29. The method of embodiment 26, wherein the contacting step comprises contacting the test sample with a plurality of functionalized beads in a reaction solution, wherein the functionalized beads are present in the reaction solution in a concentration that ranges from about 10 to about 1,000 per μl.

Embodiment 30. The method of embodiment 26, wherein contacting step comprises contacting the test sample with a solution comprising a plurality of functionalized beads, wherein the functionalized beads are present in an amount such that the amount ratio of the target microparticle to the functionalized beads ranges from 5 to 10e9.

Embodiment 31. The method of any one of embodiments 12-30, where after an initial analysis based on scatter and/or fluorescence signals, the method comprises using Boolean logic to automatically adjust and optimize the concentration the functionalized beads, the concentration of microparticles in the test sample, or the concentration of the secondary reagent.

Embodiment 32. The method of embodiment 31, wherein the optimizing includes optimizing the concentration ratio between the functionalized beads and the microparticles in the test sample.

Embodiment 33. A method of screening for a compound that can block a target microparticle contained in a test sample from binding to its cognate receptor, the method comprises: contacting the test sample containing the target microparticle with a plurality of functionalized beads and a potential blocking agent to produce a treated test sample, wherein the size of the target microparticle is less than 2 μm, wherein the functionalized beads comprise beads coated with the cognate receptor molecules, and wherein the binding of the functionalized beads to the target microparticle results in a signal that is a detectable by flow cytometer; and (b) analyzing the treated test sample using a flow cytometer, and (c) determining the blocking agent can block binding of the microparticle to its cognate receptor if the signal resulted from binding of the functionalized beads to the target microparticle is not detected, or determining the blocking agent cannot block binding of the microparticle to its cognate receptor if the signal resulted from binding of the functionalized beads to the target microparticle is detected.

Embodiment 34. The method of any one of embodiments 1-33, wherein the test sample is a throat swab sample, a nasal swab sample, or a sputum sample from a patient.

Embodiment 35. A method of detecting at least two different target microparticles in a test sample, the method comprising: (a) contacting the test sample with a plurality of functionalized beads, wherein the functionalized beads comprise beads coated with at least two capture agents, each recognizing a different target microparticle, wherein, for each of the capture agents, at least some molecules of the capture agent bind to their cognate target microparticle, thereby forming target microparticle-loaded beads comprising the functionalized beads and the cognate target microparticle, thereby forming at least two different target microparticle-loaded beads; and (b) detecting the at least two different target microparticle-loaded beads using a flow cytometer, thereby detecting the presence of the at least two different target microparticles in the test sample.

Embodiment 36. The method of embodiment 35, wherein the at least two different target microparticle-loaded beads are capable of producing fluorescence that can be detected at different detection channels of the flow cytometer.

Embodiment 37. The method of embodiment 35 or 36, wherein the at least two different target microparticles comprise a SARS-COV-2 virus and an influenza virus.

Embodiment 38. A kit for detecting a target microparticle in a test sample, wherein the kit comprises a plurality of functionalized beads, wherein each of at least some of the functionalized beads is coated with one or more capture agents; and wherein the one or more capture agents are capable of binding to the target microparticle.

Embodiment 39. The kit of embodiment 38, wherein the kit further comprises a secondary reagent, wherein the secondary reagent is capable of binding to the target microparticle, and said binding produces a detectable signal in a detection channel of a flow cytometer.

Embodiment 40. The kit of embodiment 38 or 39, wherein the plurality of functionalized beads emit fluorescence, and wherein the kit further comprises a quencher, wherein the quencher is capable of binding to the functionalized beads, and wherein said binding quenches the fluorescence in the absence of the target microparticle.

Embodiment 41. A system for detecting target microparticle in a test sample, wherein the system comprises: a component for loading the test sample, a plurality of functionalized beads, wherein each of the at least some functionalized bead is coated with one or more capture agents, wherein one or more capture agents are capable of binding to the target microparticles; and a flow cytometer for detecting the binding between the target microparticle and the functionalized beads.

Embodiment 42. A method of detecting a target micropar-
ticle in more than one test samples, wherein the more
than one test samples comprise a first test sample and
a second test sample, the method comprising: (a) con-
tacting the first test sample with first functionalized
beads, and contacting the second test sample with
second functionalized beads, wherein the first function-
alized beads and the second functionalized beads are
distinguishable in size, fluorescence characteristics, or
a combination of both, wherein the first and the second
functionalized beads are coated with a capture agent
recognizing the target microparticle, wherein at least
some molecules of the capture agent in the first func-
tionalized beads bind to the target microparticle in the
first test sample to form first target microparticle-
loaded beads, and wherein at least some molecules of
the capture agent in the second functionalized beads
bind to the target microparticle in the second test
sample to form second target microparticle-loaded
beads, (b) combining the first target microparticle-
loaded beads and the second target microparticle-
loaded beads in one single reaction, and (c) detecting
the first and the second target microparticle-loaded
beads, thereby detecting the presence of the target
microparticles in the first test sample and the second
test sample, respectively.

EXAMPLES

The following examples are offered to illustrate, but not
to limit the claimed invention.

Example 1. Bead Selection

This investigation aims to assess the viral capture perfor-
mance of several sets of beads that have been carboxyl-
functionalized to covalently link the capture moiety of
interest. Assessment of autofluorescence will be determined
using six laser wavelengths ranging from near UV to the
Infra-red region to limit emission bleed into the RNA
specific dye channel and aide in optimizing bead isolation
gating. The following bead sizes will be evaluated.

| Size | Composition | Functional Group |
| --- | --- | --- |
| 600 nm | Latex | —COOH |
| 1 um | Latex | —COOH |
| 4 um | Latex | —COOH |
| 5 um | Latex | —COOH |

Spiking studies into negative nasal swab collections will
be evaluated to ensure minimization of non-specific agglu-
tination for the different size capture beads. Predefined bead
concentrations will be injected and analyzed and singlet
enumeration will be evaluated based on forward scatter.

Example 2. Bead Functionalization

Carboxyl-functionalized microsphere will be employed
for covalent coupling of the anti-S protein peptide. EDAC-
mediated coupling is a well-established methodology for
covalent surface coating of polystyrene.

Anti-spike(S) protein Synthetic Peptide: Recent publica-
tion by Zhang, et al (8) assessed the association of a
synthetic xenoprotein peptide with the receptor binding
domain (RBD) of SARS-COV-2.

| Bead | Protein Concentration |
| --- | --- |
| 1 um | 15 mg/g bead (saturation) |
| 1 um | 1.5 mg/g bead |
| 2 um | 30 mg/g bead (saturation) |
| 2 um | 3 g/g bead |
| 4 um | 60 mg/g bead (saturation) |
| 4 um | 6.0 mg/g bead |
| 5 um | 75 mg/g bead (saturation) |
| 5 um | 7.5 mg/g bead |

The purpose of the differing protein concentrations is to
assess binding kinetics relative to viral particle concentra-
tion and the level of binding capacity per bead. For example,
during the spiking experiments it may be found that higher
levels of protein functionalization per bead may lower
binding capacity due to steric factors. Additionally, optimi-
zation of fluorescence due to the RNA-specific dye needs to
be optimized per bead event through the cytometer by
potentially increasing binding capacity and therefore
increasing the number of viral particles bound per bead. The
effect of increased viral particle capture translates to higher
fluorescence per bead unit when analysis of the RNA dye is
performed. See FIG. 2

Example 3. Bead Concentration

Optimization of bead concentration per assay will be
performed in spiking studies utilizing standard viral trans-
port media. Briefly, serial dilutions of viral particles will be
assessed against predefined bead populations deposited into
the sample at a 10× concentration. Reductions in expected
bead concentration in the singlet gate will be assessed and
compared to a negative control with the same bead concen-
tration.

While data is emerging, several recent publications have
shown viral loads in nasal, sputum, and throat swabs to have
lower limits, based on cycle threshold (Ct) values, around
$10^4$/ml (Pan et al. 2020, Zou et al. 2020). With this clinical
variable in mind an analytical limit of detection (LoD) of
$1 \times 10^3$ viral particles per ml of vital transport media func-
tionalized beads will be added to the 3 ml sample volume
and incubated for 15 minutes. Total reaction bead counts for
the 3 ml sample will be 100, 1000, 10,000, and 100,000. The
3 ml sample will be spun to pull down the functionalized
beads and resuspended in 100 µl of PBS. This investigation
will be used to define the singlet bead gating strategy for
subsequent evaluations and help define bead population
statistics with particular attention being paid to doublet
formation due to non-specific bead agglutination.

| Total Bead Deposition (Pre-centrifugation) | Expected Bead Enumeration (20 ul Injection) |
| --- | --- |
| 100 | 20 |
| 1000 | 200 |
| 10,000 | 2000 |
| 100,000 | 20,000 |

Additionally, using an analytical limit of detection (LoD)
of $1 \times 10^3$ viral particles per ml of viral transport media and
a sample volume per assay of 250 ul the minimum viral load
per assay well is 250 SARS-COV-2 particles. The following
working bead concentrations will be evaluated directly out
of the sample (without centrifugation):

| Bead Concentration | Total Bead Population (20 ul injection) |
|---|---|
| 10/ul | 200 |
| 50/ul | 1000 |
| 100/ul | 2000 |
| 500/ul | 10,000 |

Gating strategy and population statistics will be determined in triplicate for 20 negative samples to determine matrix effects on CV for scatter parameters of the bead population. This data will be utilized to determine threshold characteristics for positive samples. Additionally, autofluorescence parameters will be assessed for appropriate channels of the cytometer.

Example 4. Sars-COV-2 Spiking Studies

Each of the two previously described methods of bead evaluation (with and without centrifugation) as well as the four previously described bead concentrations will be evaluated with the following viral particle concentrations to assess the effect of virion binding on bead population statistics:

| Viral Particle Concentration/ml | Assessed Parameters |
|---|---|
| 0 | Singlet enumeration, Side scatter mean/CV, Forward scatter mean/CV, Doublet, Triplet enumeration |
| $10^2$ | Singlet enumeration, Side scatter mean/CV, Forward scatter mean/CV, Doublet, Triplet enumeration |
| $10^3$ | Singlet enumeration, Side scatter mean/CV, Forward scatter mean/CV, Doublet, Triplet enumeration |
| $10^4$ | Singlet enumeration, Side scatter mean/CV, Forward scatter mean/CV, Doublet, Triplet enumeration |
| $10^5$ | Singlet enumeration, Side scatter mean/CV, Forward scatter mean/CV, Doublet, Triplet enumeration |
| $10^6$ | Singlet enumeration, Side scatter mean/CV, Forward scatter mean/CV, Doublet, Triplet enumeration |

Example 5. Secondary Characteristic Evaluation: RNA/Lipid Elucidation

The RNA-specific dye Acridine Orange (AO) will be evaluated for fluorescence intensity relative to bead capture. AO is a cell-permeant intercalating dye that emits at two different wavelengths based on DNA or RNA binding. AO exhibits a large Stokes shift with emission in the 650 nm peak range when bound to RNA.

Briefly, gating strategy will include the identification of relevant bead populations including doublet and triplet gates. Orthogonal analysis will evaluate the quantitative 650 nm emission for the range of viral particle concentrations. Particular attention will be paid to establishing the Limit of Blank (LoB) to aid in establishing a working threshold for positivity.

Acridine Orange Testing Concentrations
  0 nM (non-intercalated autofluorescence @ 650 nm)
  500 nM
  1 uM
  2 uM Viral Particle Concentrations for Testing
  $10^7$/ml
  $10^5$/ml
  $10^3$/ml
  $10^2$/ml
  $10^0$/ml AO optimization will begin by utilizing the fluorimeter function on the Shero Diagnostics Automated Sana platform, which enables measuring the fluorescence signal associated with bulk sample rather than discrete particles. In this case, the Sana platform effectively functions as an ultrasensitive fluorimeter during the development process. Briefly, emission spectra near the 650 nm range will be evaluated to optimize viral tagging at the low end of the proposed detection limit of $10^3$ viral particles per milliliter. This includes both AO concentration and the necessity of envelope permeabilization with detergents. Subsequent AO parameters will then be tested on upper limits of viral load to ensure adequate RNA tagging when high viral titers are present.

DiO is a lipophilic carbocyanine dye that is only weakly fluorescent when unbound but emits a large signal when associated with lipid membranes.

DiO Testing Concentrations
  0 nM (non-intercalated autofluorescence @ approximately 500 nm)
  500 nM
  1 uM
  2 uM

Example 6. Analytical Performance Data

Two data sets will be created similar to the previously described bead enumeration data. Briefly, optimized AO will be added to samples spiked with SARS-COV-2 across a range of viral loads.

| Pre-Analysis Centrifugation | | |
|---|---|---|
| Viral Load | Total Bead Deposition | Parameters |
| 0 | $10^2$, $10^3$, $10^4$, $10^5$ | Singlet Enumeration, Total Bead Fluorescence |
| $10^2$/ml | $10^2$, $10^3$, $10^4$, $10^5$ | Singlet Enumeration, Total Bead Fluorescence |
| $10^3$/ml | $10^2$, $10^3$, $10^4$, $10^5$ | Singlet Enumeration, Total Bead Fluorescence |
| $10^5$/ml | $10^2$, $10^3$, $10^4$, $10^5$ | Singlet Enumeration, Total Bead Fluorescence |
| $10^7$/ml | $10^2$, $10^3$, $10^4$, $10^5$ | Singlet Enumeration, Total Bead Fluorescence |

| Direct Analysis Without Centrifugation | | |
|---|---|---|
| Viral Load | Bead Concentration | Parameters |
| 0 | 10, 50, 100, 500/ul | Singlet Enumeration, Total Bead Fluorescence |
| $10^2$/ml | 10, 50, 100, 500/ul | Singlet Enumeration, Total Bead Fluorescence |
| $10^3$/ml | 10, 50, 100, 500/ul | Singlet Enumeration, Total Bead Fluorescence |
| $10^5$/ml | 10, 50, 100, 500/ul | Singlet Enumeration, Total Bead Fluorescence |
| $10^7$/ml | 10, 50, 100, 500/ul | Singlet Enumeration, Total Bead Fluorescence |

Example 7. Detecting Microparticles in a Patient

Samples (sputum, blood, urine, oropharyngeal swab, or nasopharyngeal swab) from patients who are suspected of being exposed to SARS-COV-2 viruses are treated with a sample diluent, surfactant, or a washing agent and placed in a transport media to ensure stability. Samples are loaded to a cartridge which has been preloaded with required reagents, including functionalized beads, and an RNA intercalating dye. The cartridge with samples is inserted into the Shero Diagnostics Automated Sana platform. The Sana platform has the requisite bulk fluids, sheath fluid, sterilization fluid, washing buffer, analysis buffer, surfactant, diluent and other required components of the assay on board. The Sana platform then automatically executes all pre-analytical sample preparation steps, which include centrifugation, lysis, washing, dilution, reagent addition, incubation, and liquid handling.

The data from the Sana platform will be used for a preliminary screening of samples, which measures the background noise and determines signal level based on functionalized beads that have not been exposed to patient samples on all necessary scatter and fluorescence channels. The preliminary screening also includes measuring native auto-fluorescence of the capture beads, and determining singlet, doublet, triplets based on the appropriate signal height vs signal area and or width parameters which may impact the signal on the detection channel associated with the RNA intercalating agent. In some embodiments, a control sample that has displayed positive signal in the same fluorescence channel as the test sample is used to assist with the analysis. This control sample can be, for example, a deactivated target microparticle that retains the ability to bind to the capture agent on the functionalized beads, or a different bead which emits in the same range as the secondary reagent. A threshold for the signal in the fluorescence channel is then determined, where a signal from the detection channel sufficiently greater than the threshold indicates the unequivocal presence of the target microparticles. The system will then acquire and analyze a sample exposed and bound to capture beads. Data will be analyzed based on predetermined thresholds used to diagnose the presence of microparticles. If the data are unequivocal (showing that the target microparticle is present), the analysis is completed. If the data is equivocal (i.e., the signal from the detection channel is not sufficiently greater than the threshold) the system will use Boolean logic (as described in U.S. Pat. No. 10,338,897) based on predetermined metrics to make necessary changes to the assay including but not limited to changing and optimizing the bead to microparticle ratio or changing and optimizing the dye and/or antibody to microparticle ratio. See FIG. 5. Samples with new preparation will be re-acquired and analyzed based on scatter, auto-fluorescence and fluorescence signals. The system will repeat previous steps if necessary, to continue optimization until data falls within an unequivocal range. The system will then display results from each acquisition along with optimization steps. In some embodiments, if the signal from the test sample is greater, but not sufficiently greater, than the threshold, the system uses the Boolean logic to optimize assay conditions and run a predetermined number of iterations of the assay under these optimized conditions. If the results from these iterations are unequivocal, the test sample is reported as positive for the target microparticle; otherwise, the test sample is reported as equivocal. In some embodiments, if the signal from the test sample is less than the threshold, the system also uses the Boolean logic to optimize assay conditions and run a predetermined number of iterations of the assay under these optimized conditions. If the results from these iterations are all negative, the result of the test sample is reported as negative. The predetermined number of iterations can be, e.g., at least 2, at least 3, at least 4, or at least 5 iterations. Exemplary components used in the present disclosure are shown in FIG. 4.

Example 8. Detecting Microparticles in a Patient

Samples (sputum, blood, urine, oropharyngeal swab, or nasopharyngeal swab) from multiple patients who are suspected of being exposed to SARS-COV-2 viruses are collected in sample collection vials, one sample per vial. These vials are preloaded with functionalized beads with unique identification characteristics (e.g., size and/or fluorescence characteristics, or a combination of both). Thus, each sample can be uniquely identified based on the identification characteristics of the functionalized beads in the vial. With the incorporation of unique identification characteristics, a plurality of samples can be combined, processed, loaded on the cassette, and analyzed as described in Example 7.

Figure 6:
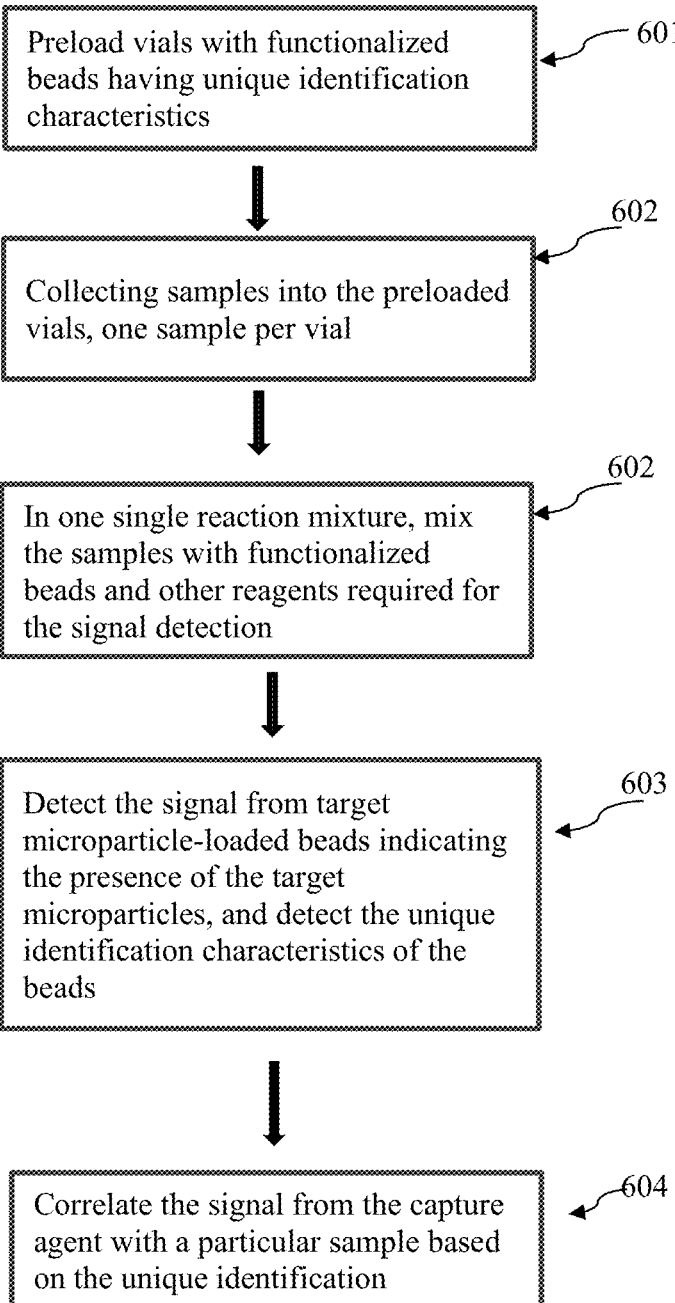
FIG. 6 illustrates an exemplary work flow of a multiplex assay detecting the presence of the target microparticles in multiple patient samples in one single reaction.

In some cases, each preloaded collection vial as described above has a patient identification barcode printed thereon, and each patient identification barcode is mapped to the unique identification characteristics of the functionalized beads. A positive signal from a single reaction containing a mixture of multiple patient samples can be traced to specific individual(s) by correlating the specific bead characteristic to the barcode on the vial and the patient. An exemplary workflow of this multiplex assay is shown in FIG. 6.

This multiplex approach allows for rapid, high-throughput screening of patent samples.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of detecting a target microparticle in a test sample, the method comprising:

(a) binding a plurality of functionalized beads to a compound that reduces a detectable signal resulting from binding of a secondary reagent to the plurality of functionalized beads,
wherein the plurality of functionalized beads is coated with molecules of a capture agent that binds the target microparticle,
wherein the detectable signal is emitted by the secondary reagent in a detection channel of a flow cytometer, and
wherein the secondary reagent binds to the plurality of functionalized beads and to the target microparticle in a nonspecific manner;

(b) after step (a), contacting the test sample containing the target microparticle with the plurality of functionalized beads, thereby forming target microparticle-loaded beads comprising the plurality of functionalized beads and the target microparticle
wherein the size of the target microparticle is less than 1 μm;

(c) contacting the target microparticle with the secondary reagent; and (d) detecting the target microparticle-loaded beads using the flow cytometer, thereby detecting a presence of the target microparticle in the test sample, wherein the target microparticle-loaded beads are detected with a detection limit that ranges from 10 microparticles per ml to $10^4$ microparticles per ml.

2. The method of claim 1, wherein contacting the target microparticle with the secondary reagent comprises contacting the test sample with the secondary reagent before step (b), or contacting the target microparticle-loaded beads with the secondary reagent after step (b) but before step (d).

3. The method of claim 1, wherein the target microparticle is a SARS-COV-2 viral particle, wherein the viral particle comprises membrane lipids and nucleic acids, and wherein the secondary reagent intercalates to the nucleic acids or the membrane lipids.

4. The method of claim 1, wherein the secondary reagent is a member selected from the group consisting of a cell-permeant, an RNA-specific dye or a lipophilic carbocyanine dye.

5. The method of claim 1, wherein the plurality of functionalized beads is capable of emitting a detectable signal, wherein the compound of step (a) comprises a quencher, wherein the quencher is capable of binding to the plurality of functionalized beads in the absence of the target microparticle, and wherein step (a) quenches and/or attenuates the detectable signal from the plurality of functionalized beads.

6. The method of claim 5, wherein the quencher binds to the plurality of functionalized beads with less affinity than the target microparticle does, and/or the quencher binds to the plurality of functionalized beads through binding to the molecules of the capture agent on the plurality of functionalized beads.

7. The method of claim 6 where presence of the target microparticle in the test sample displaces the quencher from binding to the plurality of functionalized beads.

8. The method of claim 2, wherein detecting the target microparticle-loaded beads in the test sample comprises:

(1) (i) analyzing a calibration sample comprising calibration functionalized beads with or without the secondary reagent using the flow cytometer, wherein the calibration functionalized beads are of the same type as the plurality of functionalized beads used to contact the test sample in step (b), and wherein the calibration sample does not comprise the target microparticle, (ii) collecting signals from scatter and/or fluorescence channels of the flow cytometer, (iii) determining relative positions of the calibration functionalized beads in a flow cytometry plot displaying data from the scatter and/or fluorescence channels, and selecting at least one gate that includes the calibration functionalized beads and excludes other particles, and (iv) determining a threshold that is greater than the signal from the detection channel for the calibration sample based on the at least one gate;

(2) analyzing the test sample that has contacted the plurality of functionalized beads using the flow cytometer; and (3) detecting the signal generated from the detection channel for the test sample that has contacted the plurality of functionalized beads based on the at least one gate, wherein the signal is sufficiently greater than the threshold, thereby detecting the target microparticle.

9. The method of claim 6, wherein detecting the target microparticle-loaded beads in the test sample comprises:

(1) (i) analyzing a calibration sample comprising calibration functionalized beads and the quencher using the flow cytometer, wherein the calibration functionalized beads are of the same type as the plurality of functionalized beads used to contact the test sample in step (b), and wherein the calibration sample does not comprise the target microparticle, (ii) collecting signals from scatter and/or fluorescence channels of the flow cytometer, (iii) determining relative positions of the calibration functionalized beads in a flow cytometry plot displaying data from the scatter and/or fluorescence channels, and selecting a gate that includes the calibration functionalized beads and excludes other particles, and (iv) determining a threshold that is greater than the signal from the detection channel of the flow cytometer for the calibration sample based on the gate;

(2) analyzing the test sample that has contacted the plurality of functionalized beads using the flow cytometer; and (3) detecting the signal generated from the detection channel for the test sample that has contacted the plurality of functionalized beads based on the gate, wherein the signal is sufficiently greater than the threshold, thereby detecting the target microparticle.

10. The method of claim 1, wherein the target microparticle is a member selected from the group consisting of a virus, a bacterium, a minicell, an exosome, and a microvesicle.

11. The method of claim 1, wherein the target microparticle is present in the test sample in a concentration that ranges from about 10 to about $10^7$ of the target microparticle per milliliter.

12. The method of claim 2, wherein:

i) the plurality of functionalized beads has an average diameter of 10 nm to 10,000 nm; and/or ii) 1% to 100% of the surface of the plurality of functionalized beads is covered with the molecules of the capture agent; and/or iii) the plurality of functionalized beads is coated with an average of 1-106 capture agent molecules; and/or iv) the plurality of functionalized beads is capable of emitting fluorescence.

13. The method of claim 1, wherein the capture agent has one or more of the following features:

i) being a member selected from the group consisting of a polypeptide, an antibody or binding portion thereof, a nucleic acid, an aptamer, and a phage;

ii) being linked to the plurality of functionalized beads through non-covalent coupling or covalent linkage.

14. The method of claim 1, wherein contacting the test sample with the plurality of functionalized beads comprises incubating the test sample with the plurality of functionalized beads for a period of time that ranges from about 1 to about 60 minutes.

15. The method of claim 1, wherein step (b) comprises contacting the test sample with the plurality of functionalized beads in a reaction solution, wherein the plurality of functionalized beads is present in the reaction solution in a concentration that ranges from about 10 to about 1,000 per µl, and/or the plurality of functionalized beads is present in an amount such that the amount ratio of the target microparticle to the plurality of functionalized beads ranges from 5:1 to $10^9$:1.

16. The method of claim 8, wherein after an initial analysis based on scatter and/or fluorescence signals, the method comprises using Boolean logic to automatically adjust and optimize the concentration the plurality of functionalized beads, the concentration of the target microparticle in the test sample, or the concentration of the secondary reagent.

17. The method of claim 16, wherein the optimizing includes optimizing a concentration ratio between the plurality of functionalized beads and the target microparticle in the test sample.

18. The method of claim 1, wherein the test sample is a throat swab sample, a nasal swab sample, or a sputum sample from a patient.

19. The method of claim 1, wherein the target microparticle is a first target microparticle and the test sample further comprises a different second target microparticle;

wherein step (b) further comprises contacting the test sample with a plurality of second functionalized beads coated with molecules of a second capture agent that binds the second target microparticle, thereby forming second target microparticle-loaded beads comprising the plurality of second functionalized beads and the second target microparticle; and wherein step (d) further comprises detecting the second target microparticle-loaded beads using the flow cytometer, thereby detecting a presence of the second target microparticle in the test sample.

20. The method of claim 19, wherein the detection channel is a first detection channel, and wherein the second target microparticle-loaded beads are capable of producing fluorescence that can be detected at a second detection channel of the flow cytometer different from the first detection channel.

21. The method of claim 1, wherein the test sample is a first test sample, the plurality of functionalized beads is a plurality of first functionalized beads, and the target microparticle-loaded beads are first target microparticle-loaded beads;

wherein step (b) further comprises contacting a second test sample with a plurality of second functionalized beads;

wherein the plurality of first functionalized beads and the plurality of second functionalized beads are distinguishable in size, fluorescence characteristics, or a combination of both;

wherein the plurality of second functionalized beads is coated with molecules of a second capture agent that binds the target microparticle, wherein the contacting of the second test sample with the plurality of second functionalized beads forms second target microparticle-loaded beads comprising the plurality of second functionalized beads and the target microparticle;

wherein the method further comprises combining the first target microparticle-loaded beads and the second target microparticle-loaded beads in one single reaction; and wherein step (d) comprises detecting the first and the second target microparticle-loaded beads, thereby detecting a presence of the target microparticle in the first test sample and the second test sample, respectively.

\* \* \* \* \*